United States Patent
Lee et al.

(10) Patent No.: US 9,335,331 B2
(45) Date of Patent: May 10, 2016

(54) MULTIPLEXED BIOMARKERS FOR MONITORING THE ALZHEIMER'S DISEASE STATE OF A SUBJECT

(75) Inventors: Kelvin H. Lee, Newark, DE (US); Norman R. Relkin, Harrington Park, NJ (US); Erin Finehout, Kensington, MD (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1344 days.

(21) Appl. No.: 11/910,721

(22) PCT Filed: Apr. 10, 2006

(86) PCT No.: PCT/US2006/013234
§ 371 (c)(1),
(2), (4) Date: Sep. 22, 2008

(87) PCT Pub. No.: WO2006/110621
PCT Pub. Date: Oct. 19, 2006

(65) Prior Publication Data
US 2009/0075395 A1    Mar. 19, 2009

Related U.S. Application Data

(60) Provisional application No. 60/669,897, filed on Apr. 11, 2005.

(51) Int. Cl.
*G01N 33/68* (2006.01)
*G01N 33/563* (2006.01)
*G06F 17/30* (2006.01)

(52) U.S. Cl.
CPC .... *G01N 33/6896* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 4,837,164 A | 6/1989 | Glick | |
| 5,508,167 A | 4/1996 | Roses et al. | |
| 5,747,260 A | 5/1998 | Roberts et al. | |
| 5,942,392 A | 8/1999 | Amouyel et al. | |
| 5,958,684 A | 9/1999 | Van Leeuwen et al. | |
| 6,027,896 A | 2/2000 | Roses et al. | |
| 7,052,852 B1 | 5/2006 | Mullan et al. | |
| 2002/0052311 A1 | 5/2002 | Solomon et al. | |
| 2002/0064773 A1 | 5/2002 | Herrnstadt et al. | |
| 2002/0086290 A1 | 7/2002 | Sevigny et al. | |
| 2002/0098173 A1 | 7/2002 | Findeis et al. | |
| 2002/0098481 A1 | 7/2002 | Einstein et al. | |
| 2002/0115717 A1 | 8/2002 | Gervais et al. | |
| 2002/0137108 A1 | 9/2002 | Mullan et al. | |
| 2002/0150948 A1 | 10/2002 | Castillo et al. | |
| 2003/0162207 A1 | 8/2003 | Comings et al. | |
| 2003/0170678 A1 | 9/2003 | Tanzi et al. | |
| 2003/0215880 A1 | 11/2003 | Burton et al. | |
| 2003/0224380 A1 | 12/2003 | Becker et al. | |
| 2003/0233035 A1 | 12/2003 | Rubenstein | |
| 2004/0005307 A1 | 1/2004 | Findeis et al. | |
| 2004/0013680 A1 | 1/2004 | Bush et al. | |
| 2004/0022794 A1 | 2/2004 | Durham et al. | |
| 2004/0072261 A1 | 4/2004 | Kostanjevecki et al. | |
| 2004/0081652 A1 | 4/2004 | Zack et al. | |
| 2004/0086511 A1 | 5/2004 | Zack et al. | |
| 2004/0096896 A1 | 5/2004 | Agus et al. | |
| 2004/0101867 A1 | 5/2004 | Fritzsche | |
| 2004/0157267 A1 | 8/2004 | Huang | |
| 2004/0180048 A1 | 9/2004 | Zack et al. | |
| 2004/0209379 A1 | 10/2004 | Bar-Or et al. | |
| 2004/0248197 A1 | 12/2004 | Holtzman et al. | |
| 2005/0048000 A1 | 3/2005 | Gervais et al. | |
| 2005/0048547 A1 | 3/2005 | Zhao et al. | |
| 2005/0196794 A1 | 9/2005 | Nurnberg et al. | |
| 2005/0244890 A1 | 11/2005 | Davies et al. | |
| 2005/0260767 A1 | 11/2005 | Clerici et al. | |
| 2005/0266501 A1 | 12/2005 | Ota et al. | |
| 2006/0024759 A1 | 2/2006 | Holtzman | |

OTHER PUBLICATIONS

Merril et al., Applied and Theoretical Electrophoresis, 5:49-54, 1995.*
Zhang et al., Neurobiology of Aging, 26: 207-227, Feb. 2005.*
Davidsson et al., Mol Brain Res, 109:128133, 2002.*
Finehout et al., Disease Markers, 21:93-101, May 26, 2005.*
Shuvaev et al., Neurobiol of Aging, 22:397-402, 2001.*
Puchades et al., Mol Brain Res, 118:140-146, 2003.*
Choe et al., Electrophoresis, 23, 2247-2251 (2002).*
Random Forests. Published [online] at <http://www.stat.berkeley.edu/~breiman/RandomForests/cc_home.htm> published May 10, 2004. Retreived [online] on Oct. 20, 2014 from WAYBACK machine <https://web.archive.org/web/20040510073250/http://www.stat.berkeley.edu/~breiman/RandomForests/cc_home.htm>.*
Link et al., Nature vol. 17: 676-682, Jul. 1999.*
International Search Report for corresponding International Patent Application No. PCT/US06/13234 (Jun. 24, 2010).
Puchades et al., "Proteomic Studies of Potential Cerebrospinal Fluid Protein Markers for Alzheimer's Disease," Molecular Brain Res. 118(1-2):140-6 (2003) (Abstract).
Written Opinion of the International Searching Authority for corresponding International Patent Application No. PCT/US06/13234 (Jun. 10, 2010).

* cited by examiner

*Primary Examiner* — Daniel E Kolker
*Assistant Examiner* — Stacey N MacFarlane
(74) *Attorney, Agent, or Firm* — LeClairRyan, a Professional Corporation

(57) ABSTRACT

The present invention relates to a method for diagnosing a subject's Alzheimer's disease state. The method involves providing a database containing information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. Information relating to proteins found in one or more cerebrospinal fluid samples from a subject is also provided and a database is used to analyze the information from the subject to diagnose the subject's Alzheimer's disease state. Also disclosed is a computer readable medium and a system, both useful in carrying out the present invention.

11 Claims, 9 Drawing Sheets

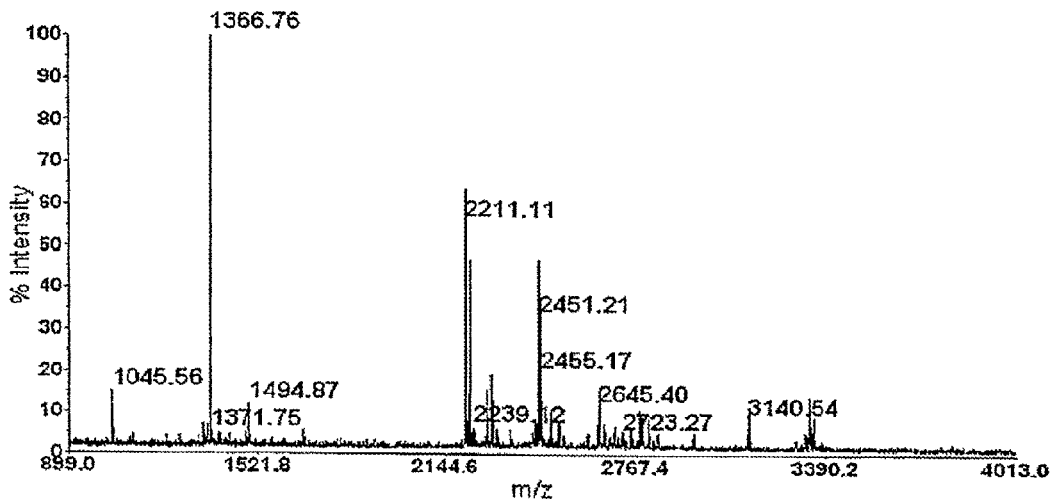
FIG. 7A
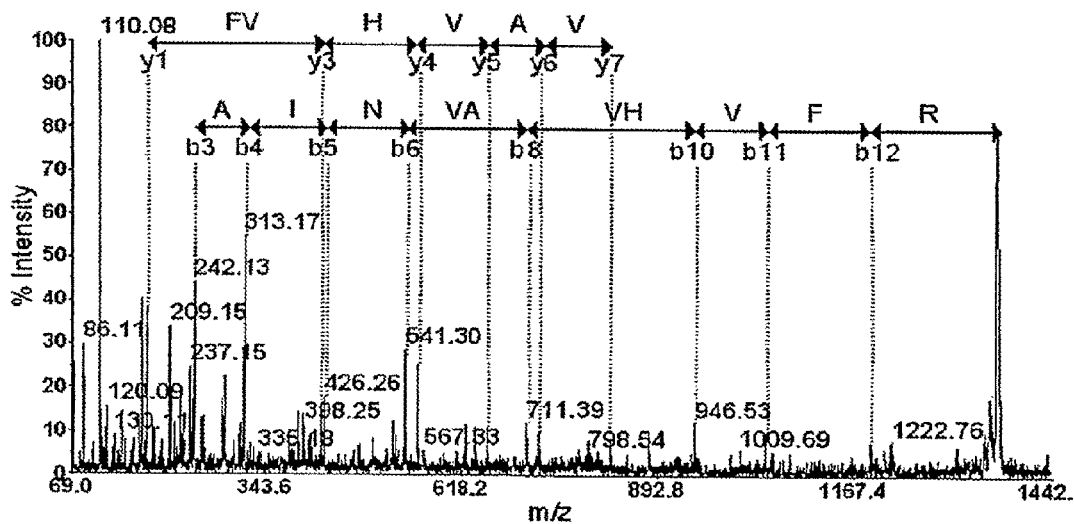
FIG. 7B
```
  1 PLMVKVLDAV  RGSPAINVAV  HVFRKAADDT  WEPFASGKTS  ESGELHGLTT
 51 EEEFVEGIYK  VEIDTKSYWK  ALGISPFHEH  AEVVFTANDS  GPRRYTIAAL
101 LSPYSYSTTA  VVTNPKE
```
FIG. 7C

MULTIPLEXED BIOMARKERS FOR MONITORING THE ALZHEIMER'S DISEASE STATE OF A SUBJECT

This application is a national stage application under 35 U.S.C. §371 of PCT/US2006/013234, filed Apr. 10, 2006, and claims the benefit of U.S. Provisional Patent Application Ser. No. 60/669,897, filed Apr. 11, 2005, which the present application hereby incorporates by reference in its entirety.

The subject matter of this application was made with support from the United States Government under The National Institutes of Health, Grant R01MH59926. The U.S. Government may have certain rights.

FIELD OF THE INVENTION

The present invention is directed to multiplexed biomarkers for monitoring the Alzheimer's disease state of a subject.

BACKGROUND OF THE INVENTION

Alzheimer's disease (AD) is the leading cause of dementia in the elderly (Cummings J L., "Cole G. Alzheimer Disease, *JAMA* 287:2335-2338 (2002)). Current antemortem methods of AD diagnosis correctly identify the disease in 80 to 90% of cases through the use of patient history, brain imaging, and neuropsychological testing at expert academic research centers (Kennard M., "Diagnostic Markers for Alzheimer's Disease," *Neurobiol Aging* 19:131-132 (1998)) but the typical clinical diagnostic accuracy is probably lower. Typically, a diagnosis cannot be made until the disease has progressed far enough that dementia is present and, even then, the patient is classified as having possible AD or probable AD (McKhann et al., "Clinical Diagnosis of Alzheimers-Disease—Report of the NINCDS-ADRDA Work Group Under the Auspices of Department of Health and Human Services Task Force on Alzheimer's Disease," *Neurology* 34:939-944 (1984)). Thus, a definitive diagnosis of AD currently requires a postmortem examination of the brain. A molecular biomarker for AD could complement current methods to increase the accuracy of diagnoses and make earlier diagnoses possible (Biomarkers Definitions Working Group, "Biomarkers and Surrogate Endpoints: Preferred Definitions and Conceptual Framework," *Clin Pharmacol Ther* 69:89-95 (2001)). Many studies have examined the cerebrospinal fluid (CSF) as a possible source for biomarkers of neurological diseases, because CSF is in direct contact with the brain and the molecular composition of CSF can reflect biochemical changes in the brain (Fishman R., "Cerebrospinal Fluid in Diseases of the Nervous System," 2ed New York: W.B. Saunders Co., (1992)).

In particular, there has been a focus on the proteins in CSF. Some AD CSF biomarker studies have focused on comparisons between AD and non-AD patients that are based on one (or a few) CSF proteins that have previously been determined to play a role in the pathogenesis of AD in the brain (Bonelli et al., "Cerebro Spinal Fluid Tissue Transglutaminase as a Biochemical Marker for Alzheimer's Disease," *Neurobiol Dis* 11:106-110 (2002); Peskind et al., "Cerebrospinal Fluid SI00B is Elevated in the Earlier Stages of Alzheimer's Disease," *Neurochem Int* 39:409-413 (2001); Hampel et al., "Discriminant Power of Combined Cerebrospinal Fluid Tau Protein and of the Soluble Interleukin-6 Receptor Complex in the Diagnosis of Alzheimer's Disease," *Brain Res* 823:104-112 (1999)). While this approach is useful for testing proposed biomarkers, it does not allow for new biomarker discovery. To complement this approach, other studies have compared the entire proteome of CSF between AD and non-AD patients to look for differences in protein expression. The proteome is defined as the protein complement to the genome and includes information about the proteins and peptides present, and their expression levels. Previous studies have examined the CSF proteome for AD biomarkers using several different techniques (Carrette et al., "A Panel of Cerebrospinal Fluid Potential Biomarkers for the Diagnosis of Alzheimer's Disease," *Proteomics* 3:1486-1494 (2003); Davidsson et al., "Proteome Analysis of Cerebrospinal Fluid Proteins in Alzheimer Patients," *Neuroreport* 13:611-615 (2002); Puchades et al., "Proteomic Studies of Potential Cerebrospinal Fluid Protein Markers for Alzheimer's Disease," *Brain Res Mol Brain Res* 118:140-146 (2003); Choe et al., "Studies of Potential Cerebrospinal Fluid Molecular Markers for Alzheimer's Disease," *Electrophoresis* 23:2247-2251 (2002)). Carrette et al. (Carrette et al., "A Panel of Cerebrospinal Fluid Potential Biomarkers for the Diagnosis of Alzheimer's Disease," *Proteomics* 3:1486-1494 (2003)) used surface-enhanced laser desorption/ionization (SELDI) coupled with time-of-flight (TOF) mass spectrometry (MS) to characterize the antemortem CSF proteome of nine AD patients and ten non-AD patients. The AD patients had a diagnosis of probable AD (no postmortem confirmation of diagnoses) and the non-AD patients were normal controls. The data in the Carrette study were analyzed using a Mann-Whitney U statistical test and a panel of five polypeptides were identified that could classify AD patients with a specificity of 100% and a sensitivity of 66%. In a study by Davidsson et al. (Davidsson et al., "Proteome Analysis of Cerebrospinal Fluid Proteins in Alzheimer Patients," *Neuroreport* 13:611-615 (2002)), proteins were separated by two-dimensional gel electrophoresis (2DE). The protein spots on the gel images from 15 AD patients (no postmortem confirmation of diagnoses) and 12 normal controls were compared using a Mann-Whitney U test. Fifteen protein isoforms were found to have a significant ($p<0.05$) change in their CSF concentration. In the study by Puchades et al. (Puchades et al., "Proteomic Studies of Potential Cerebrospinal Fluid Protein Markers for Alzheimer's Disease," *Brain Res Mol Brain Res* 118:140-146 (2003)), 2DE was also used to compare samples from seven AD patients (no postmortem confirmation of diagnoses) and seven normal controls using a Students t-test. Nine proteins were found to be significantly ($p<0.05$) altered between the AD and non-AD patients. Choe et al (Choe et al., "Studies of Potential Cerebrospinal Fluid Molecular Markers for Alzheimer's Disease," *Electrophoresis* 23:2247-2251 (2002)) applied multivariate statistical methods to analyze 2DE gels from ten AD patients (diagnoses confirmed postmortem), five neurologically normal patients, and two patients with Creutzfeldt-Jakob disease (CJD). Using a canonical correlation analysis, a set of nine proteins was found that could differentiate between AD and normal patients with 100% sensitivity and specificity. Using a principle factor analysis on a subset often patients (four AD, four normal, and two CJD), they found a set of 12 spots that had a sensitivity of 100% and a specificity of 83%. These studies have generated interesting preliminary data; however there are several considerations that are not completely addressed in any of the previously published work. First, antemortem CSF samples should be used and the antemortem diagnosis of AD patients should be confirmed by an autopsy. Second, neurological controls should be included in the non-AD samples. Third, a reasonably large number of CSF samples should be used and multivariate statistics should be considered for the data analysis.

An important factor in biomarker studies is the use of appropriate samples. Antemortem samples should be used for CSF biomarker studies, because there is a change in the CSF protein composition after death (Lescuyer et al., "Identification of Post-Mortem Cerebrospinal Fluid Proteins as Potential Biomarkers of Ischemia and Neurodegeneration," *Proteomics* 4:2234-2241 (2004)). The use of antemortem CSF samples from AD patients with a definitive postmortem confirmation of AD diagnosis is essential given that a significant fraction of antemortem AD diagnoses are incorrect (Kennard M., "Diagnostic Markers for Alzheimer's Disease," *Neurobiol Aging* 19:131-132 (1998)). Inclusion of incorrectly diagnosed patients would affect the reliability of the biomarkers' predicted sensitivity and specificity.

A second key element is the selection of control samples. Although a comparison of AD and normal CSF may result in the identification of biomarkers, the inclusion of neurological controls is essential for the development of clinically relevant tests. Many characteristics of AD (e.g. inflammation, memory loss, etc.) can be common to other forms of dementia and the key clinical challenge is to establish a differential diagnosis. For example, some changes in protein expression, which may be useful in segregating AD from normal, may not be useful in segregating AD from other dementias.

A third consideration is the desire to identify and validate markers from a cohort of reasonable size to better establish the statistical power of the identified markers. Prior AD proteomic studies have used between 10 and 27 total CSF samples. The larger the sample set, the more likely that the results of the statistical analysis represent the larger population. Nonetheless, the results from any preliminary dataset, including the one presented herein using 68 samples, must be validated by multiple investigators using large numbers of samples.

Finally, it is important to consider the application of appropriate multivariate statistical methods in the identification of biomarkers. AD is a complex disease and a multivariate statistical approach can result in biomarkers that better represent the disease's multifactorial nature. Many previous studies (Carrette et al., "A Panel of Cerebrospinal Fluid Potential Biomarkers for the Diagnosis of Alzheimer's Disease," *Proteomics* 3:1486-1494 (2003); Davidsson et al., "Proteome Analysis of Cerebrospinal Fluid Proteins in Alzheimer Patients," *Neuroreport* 13:611-615 (2002); Puchades et al., "Proteomic Studies of Potential Cerebrospinal Fluid Protein Markers for Alzheimer's Disease," *Brain Res Mol Brain Res* 118:140-146 (2003)) have used univariate statistical methods to determine which proteins show a change in concentration between the diseased and normal states. Univariate methods assume that any single observed change in protein expression between diseased and normal patients is independent of other protein changes. Thus, these methods cannot take interactions among proteins or biochemical pathways into account. Multivariate statistical methods do not rely on variable independence and can be used to combine information from multiple variables to improve disease diagnosis (Harris R J., "A Primer of Multivariate Statistics," 3ed. Mahwah, N.J.: Lawrence Erlbaum Associates (2001)). The importance of combining information from multiple variables has already been demonstrated in AD biomarker research. Using CSF expression levels of both $A\beta_{1-42}$ and tau results in a higher sensitivity and specificity for AD diagnosis as compared to using either protein alone (Blennow K., "Cerebrospinal Fluid Protein Biomarkers for Alzheimer's Disease," *Neurorx* 1:213-225 (2004)).

One challenge in the application of proteomic analyses for AD biomarker studies is that such studies are often underspecified—there are significantly more variables than samples (i.e. more proteins than CSF samples). This situation restricts many multivariate statistical methods from being appropriately applied to proteomic data. In 2001, Brieman introduced a method for multivariate statistical analysis, the random forest (RF) method, that is based on classification trees (Breiman L., "Random Forests," *Machine Learning* 45:5-32 (2001)). The RF method can be used to analyze underspecified systems and, unlike some other multivariate methods (such as support vector machines or artificial neural networks), it can be used even when a large number of the variables are irrelevant to the classification of the samples (Izmirlian G., "Application of the Random Forest Classification Algorithm to a SELDI-TOF Proteomics Study in the Setting of a Cancer Prevention Trial," *Acad Sci* 1020:154-174 (2004)). This is important since only a small percentage of proteins may show an expression change in response to a disease. There is also a smaller effect from noise in the variables with an RF analysis compared to some other methods, because the RF method does not concentrate weight on any subset of samples (Breiman L., "Random Forests," *Machine Learning* 45:5-32 (2001)). Another feature of RF is the method's ability to measure the importance of individual variables in sample classification. This is especially relevant to proteomic systems where, as mentioned before, a large percentage of the variables may not show a change in expression. Identifying which proteins are most important in sample classification may give insight into the biology of the system (i.e. what pathways is the disease affecting) or even allow the development of an antibody-based assay for sample classification.

This new statistical method has been applied to a variety of biological studies including the analysis of protein data related to cancer diagnosis (Izmirlian G., "Application of the Random Forest Classification Algorithm to a SELDI-TOF Proteomics Study in the Setting of a Cancer Prevention Trial," *Acad Sci* 1020:154-174 (2004)) and the determination of gene mutations that lead to antibiotic resistance (Cummings M P., "Few Amino Acid Positions in rpoB are Associated with Most of the Rifampin Resistance in Mycobacterium Tuberculosis," *BMC Bioinformatics* 5:157 (2004)). RF was compared to several other multivariate statistical methods, including linear discriminant analysis, k-nearest neighbor, and support vector machines, for determining biomarkers of ovarian cancer based on the protein mass spectra of serum (Wu et al., "Comparison of Statistical Methods for Classification of Ovarian Cancer Using Mass Spectrometry Data," *BMC Bioinformatics* 19:1636-1643 (2003)). The authors found that the RF method resulted in a lower overall misclassification rate of serum samples and a more stable assessment of classification errors.

The present invention is directed to overcoming these and other deficiencies in the art.

SUMMARY OF THE INVENTION

The present invention relates to a method for diagnosing a subject's Alzheimer's disease state. This involves providing a database containing information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. Information relating to proteins found in one or more cerebrospinal fluid samples from a subject is also provided. The database is used to analyze the information from the subject to diagnose the subject's Alzheimer's disease state.

The present invention also relates to a computer readable medium having stored programmed instructions for diagnosing a subject's Alzheimer's disease state. This includes machine executable code which when executed by at least one processor, causes the processor to perform several steps. This involves providing a database containing information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. Information relating to proteins found in one or more cerebrospinal fluid samples from a subject is also provided. The database is used to analyze the information from the subject to diagnose the subject's Alzheimer's disease state.

Another aspect of the present invention relates to a system for diagnosing a subject's Alzheimer's disease state. The system includes a storage system with at least one database comprising information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. A diagnostic processing system that receives information relating to proteins found in one or more cerebrospinal fluid samples from a subject is also provided. The database in the storage system is used to analyze the information from the subject to diagnose the subject's Alzheimer's disease state.

Alzheimer's disease (AD) is the most prevalent form of dementia in the elderly and up to 20% of antemortem AD diagnoses have been found to be incorrect. The present invention identifies a panel of proteins in antemortem CSF that can be used to differentiate between samples from AD patients and samples from normal subjects and/or from neurological controls. A panel of 23 spots was identified that could be used to differentiate AD and non-AD gels, derived from AD and non-AD CSF, with a sensitivity of 94%, a specificity of 94% and a predicted classification error rate of only 5.9%. These proteins are related to the transport of β-amyloid, the inflammatory response, proteolytic inhibition, and neuronal membrane proteins. The method presented has shown promising results. This multivariate statistical study represents the largest cohort of pathologically characterized antemortem CSF samples used in an AD proteomic biomarker study published to date and suggests the possibility of developing clinically relevant diagnostic assays based on a proteomic analysis.

BRIEF DESCRIPTION OF THE DRAWINGS

FIG. 4A shows proteins associated with β-amyloid transport. FIG. 4B shows proteins associated with inflammation and immune response. FIG. 4C shows protease inhibitors. FIG. 4D shows proteins that are not identified. Apo=Apolipoprotein, RBP=Retinol binding protein, NPR=Neuronal pentraxin receptor, and VDBP=Vitamin D-binding protein.

FIG. 6A shows ROC-like curve generated by varying the cost ratio when building the classification trees. FIG. 6B shows ROC curve generated by varying the threshold percentage of votes needed to classify a 2DE gel as AD. The area under the curve was calculated to be 0.96.

FIG. 7A-C shows spectra acquired for transthyretin-1 using MALDI-TOF/TOF MS. FIG. 7A shows a peptide mass fingerprint spectrum. FIG. 7B shows a MS/MS spectrum for the peptide with mJz=1366.76 which includes amino acids 12-24 (GSPAINVAVHVFR) (SEQ ID NO:1). The detected y- and b-ion fragments are labeled. FIG. 7C shows an amino acid sequence (SEQ ID NO:2) for transthyretin (NCBI accession #339685). The highlighted amino acids are those that are included in the peptides detected in the peptide mass fingerprint MS spectrum.

DETAILED DESCRIPTION OF THE INVENTION

Figure 1:
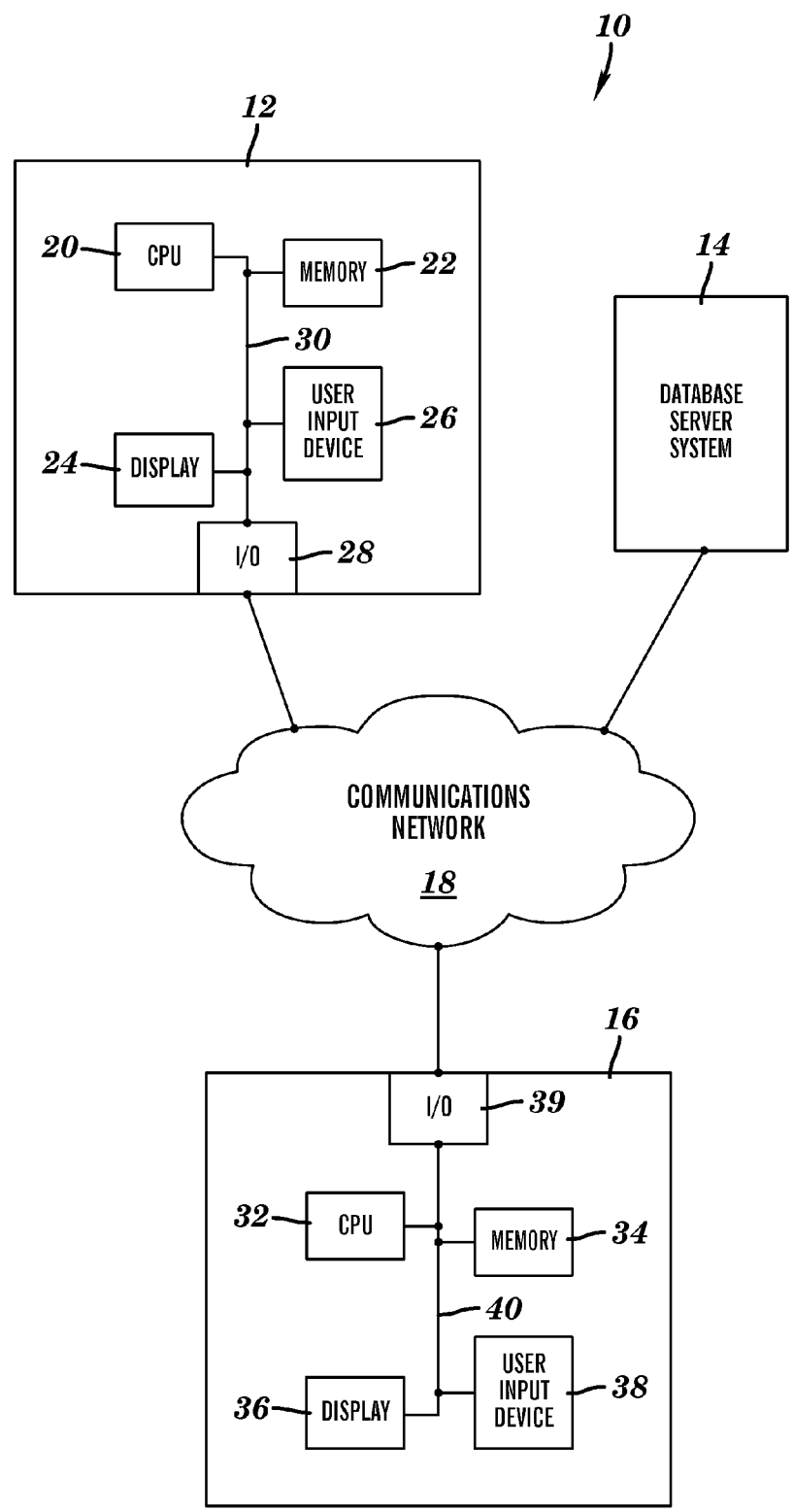
FIG. 1 is a block diagram of a system for diagnosing whether a subject has a condition in accordance with embodiments of the present invention.

The present invention relates to a method for diagnosing a subject's Alzheimer's disease state. This involves providing a database containing information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. Information relating to proteins found in one or more cerebrospinal fluid samples from a subject is also provided. The database is used to analyze the information from the subject to diagnose the subject's Alzheimer's disease state.

Suitable albumin protein spots determined by RF to be useful in differentiating AD gels from non-AD gels include albumin-1, albumin-2, and albumin-3. Albumin-1, albumin-2, and albumin-3 are present in Alzheimer's disease patients at a level of 0-0.021, 0.025-0.075, and 0-0.025 respectively, and are present in non-Alzheimer's disease at a level of 0-0.01, 0-0.025, and zero, respectively, measured as % volume relative levels between the $25^{th}$ and $75^{th}$ quartiles. See Examples 1, 2, and 4.

The form of α-1-antitrypsin can be α-1-antitrypsin-1 and α-1-antitrypsin-2. α-1-antitrypsin-1 and α-1-antitrypsin-2 are present in Alzheimer's disease patients at a level of zero and 0.025-0.05 respectively, and in non-Alzheimer's disease patients at a level of 0-0.028 and 0.015-0.025, respectively, measured as % volume relative levels between the $25^{th}$ and $75^{th}$ quartiles. See Examples 1, 2, and 4.

The apolipoprotein can be in the form of apolipoprtitein E, apolipoprotein J-1, apolipoprotein J-2, and apolipoprotein J-3. These are present in Alzheimer's disease patients at a level of 0-0.02, 0.2-0.31, 0-0.028, and 0-0.018, respectively, and in non-Alzheimer's disease patients at a level of 0-0.01, 0.18-0.28, zero, and 0-0.012, respectively, measured as % volume relative levels between the $25^{th}$ and $75^{th}$ quartiles. See Examples 1, 2, and 4.

The transthyretin-1 and transthyretin-2 are the current forms of transthyretin to be monitored. These are present in Alzheimer's disease patients at a level of 0.04-0.16 and 0-0.014, respectively, and in non-Alzheimer's disease patients at a level of 0-0.08 and 0.016-0.025, respectively, measured as % volume relative levels between the $25^{th}$ and $75^{th}$ quartiles. See Examples 1, 2, and 4.

Complement component 3 is present in Alzheimer's disease patients at a level of 0.04-0.075 and in non-Alzheimer's disease patients at a level of 0.025-0.049, measured as % volume relative levels between the $25^{th}$ and $75^{th}$ quartiles. See Examples 1, 2, and 4.

Contactin is present in Alzheimer's disease patients at a level of zero and in non-Alzheimer's disease patients at a level of 0-0.028, respectively, measured as % volume relative levels between the $25^{th}$ and $75^{th}$ quartiles. See Examples 1, 2, and 4.

Fibrin beta is present in Alzheimer's disease patients at a level of 0.005-0.035 and in non-Alzheimer's disease patients at a level of 0-0.016, measured as % volume relative levels between the $25^{th}$ and $75^{th}$ quartiles. See Examples 1, 2, and 4.

Ig heavy chain is present in Alzheimer's disease patients at a level of 0.01-0.025, and in non-Alzheimer's disease patients at a level of 0-0.02, measured as % volume relative levels between the $25^{th}$ and $75^{th}$ quartiles. See Examples 1, 2, and 4.

Ig light chain is present in Alzheimer's disease patients at a level of 0.05-0.1 and in non-Alzheimer's disease patients at a level of 0.09-0.13, measured as % volume relative levels between the $25^{th}$ and $75^{th}$ quartiles. See Examples 1, 2, and 4.

Neuronal pentraxin receptor is present in Alzheimer's disease patients at a level of 0-0.014 and in non-Alzheimer's disease patients at a level of 0.016-0.025, measured as % volume relative levels between the $25^{th}$ and $75^{th}$ quartiles. See Examples 1, 2, and 4.

Plasminogen is present in Alzheimer's disease patients at a level of 0-0.012 and in non-Alzheimer's disease patients at a level of zero, measured as % volume relative levels between the $25^{th}$ and $75^{th}$ quartiles. See Examples 1, 2, and 4.

ProSAAS is present in Alzheimer's disease patients at a level of 0.03-0.056 and in non-Alzheimer's disease patients at a level of 0.039-0.072 measured as % volume relative levels between the $25^{th}$ and $75^{th}$ quartiles. See Examples 1, 2, and 4.

Retinol-binding protein is present in Alzheimer's disease patients at a level of 0.1-0.18 and in non-Alzheimer's disease patients at a level of 0.15-0.2, measured as % volume relative levels between the $25^{th}$ and $75^{th}$ quartiles. See Examples 1, 2, and 4.

Vitamin D binding protein is present in Alzheimer's disease patients at a level of zero and in non-Alzheimer's disease patients at a level of 0-0.028, measured as % volume relative levels between the $25^{th}$ and $75^{th}$ quartiles. See Examples 1, 2, and 4.

In a preferred embodiment, the method is carried out to determine whether the subject has Alzheimer's disease or does not have Alzheimer's disease.

In another embodiment, the method is carried out to monitor the progression of disease in a subject believed to have Alzheimer's disease. Each state of the disease has a characteristic amount of a biomarker or relative amounts of a set of biomarkers. The progression of the disease is determined by measuring the relevant biomarker or biomarkers and then either submitting them to a classification algorithm or comparing them with a reference amount and/or pattern of biomarkers that is associated with the particular stage.

In another embodiment, the method involves administering a therapeutic substance to the subject as a function of the monitoring of progression of disease in the subject. Disease course refers to changes in disease status over time, including disease progression (worsening) and disease regression (improvement). Over time, the amounts or relative amounts (e.g., the pattern) of the biomarkers changes. The trend of these markers, either increased or decreased over time toward diseased or non-diseased indicates the course of the disease. In addition, this method is useful for determining response to treatment. If a treatment is effective, then the biomarkers will trend toward away from Alzheimer's disease, while, if treatment is ineffective, the biomarkers will not trend significantly away from Alzheimer's disease. The method also involves managing subject treatment based on the status of the disease by a physician or clinician.

In a preferred embodiment, information in the database is provided by obtaining proteomes of cerebrospinal fluid samples collected from subjects diagnosed with Alzheimer's disease or diagnosed as not having disease. The samples from the subjects with Alzheimer's disease are compared to the samples from the subjects without the disease. The samples are then characterized and data is generated based on the characterization. The data is then analyzed to identify a collection of proteins useful in assisting in the diagnosis of Alzheimer's disease. The proteomes of cerebrospinal fluid samples are collected from subjects diagnosed with and without Alzheimer's disease are proteomes of antemortem cerebrospinal fluid samples.

The term "cerebrospinal fluid" is meant to include serum-like fluid that circulates through the ventricles of the brain, the cavity of the spinal cord, and the subarachnoid space, functioning in shock absorption (Campbell, N., "Biology" 5ed Menlo Park, Calif., Benjamin Cummings, (1999) which is hereby incorporated by reference in its entirety).

Characterization of the samples can be conducted using two-dimensional gel electrophoresis. Analysis of the data can be conducted using the random forest method and protein identification is by mass spectrometry. The number of proteomes collected is statistically significant.

Characterization of the samples may also be conducted using immunoassays, antibodies, aptamers for the proteins as well as isoforms and fragments thereof and other comigrating proteins, isoforms, and fragments thereof, or other technologies specific to the proteins contained in the database without using two-dimensional gel electrophoresis and without using the random forest method and without using mass spectrometry The "proteome" is defined as the protein complement to the genome and includes information about the proteins and peptides present, and their expression levels.

The "random forest" method was introduced (Breiman L., "Random Forests," Machine *Learning* 45:5-32 (2001), which is hereby incorporated by reference in its entirety) as a method for multivariate analysis. It is well-suited to underspecified problems, is robust to noise in the data (biological, technical, etc.), can calculate an unbiased estimate of the classification error, and can measure the relative importance of each variable used to classify the samples.

A database is defined as a set of information about proteins that aid in the diagnosis of Alzheimer's disease based on altered expression of those proteins in CSF. A database may or may not include a computer and may or may not include a computer readable medium.

In one embodiment of the present invention, the database can be information about the positions of 23 spots on a "two-dimensional electrophoresis gel" (2DE) image. Since these spots generally won't move relative to each other in subsequent experiments, the location of the spots is potentially valuable information.

Alternatively, the database of the present invention can simply involve a listing of the proteins contained in the 23 spots of interest. The information used to establish a diagnosis may then be determined by relying on immunoassays, aptamers, and other technologies that are specific to those proteins of interest that are on the list. The identity of these proteins can be used to measure the amount of those proteins in CSF.

The database of the present invention includes a collection of proteins with a variety of presumed biological functions. These are transport of beta-amyloid, inflammation and/or immune response, proteolytic enzyme inhibitors, and neuronal membrane proteins.

The present invention also relates to a computer readable medium having stored programmed instructions for diagnosing a subject's Alzheimer's disease state. This includes machine executable code which when executed by at least one processor, causes the processor to perform several steps. This involves providing a database containing information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. Information relating to proteins found in one or more cerebrospinal fluid samples from a subject is also provided. The database is used to analyze the information from the subject to diagnose the subject's Alzheimer's disease state.

Another aspect of the present invention relates to a system for diagnosing a subject's Alzheimer's disease state. The system includes a storage system with at least one database comprising information relating to protein expression levels associated and not associated with Alzheimer's disease. The database includes information relating to at least a majority of the following proteins: albumin, alpha-1-antitrypsin, apolipoprotin E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein. A diagnostic processing system that receives information relating to proteins found in one or more cerebrospinal fluid samples from a subject is also provided. The database in the storage system is used to analyze the information from the subject to diagnose the subject's Alzheimer's disease state.

Referring more specifically to FIG. 1, the diagnostic processing system 12 diagnoses a subject's Alzheimer's disease state, although the diagnostic processing system 12 can perform other types and numbers of functions and provide other types of outputs and can be embodied in other numbers of systems. In these embodiments, the diagnostic processing system 12 comprises a central processing unit (CPU) or processor 20, a memory 22, a display 24, user input device 26, and an input/output interface system 28 which are coupled together by a bus or other link 30, although the diagnostic processing system 12 can comprise other numbers and types of components and systems in other configurations. The processor 20 executes a program of stored instructions for one or more aspects of the present invention as described and illustrated herein, including the method for diagnosing whether a subject has a condition, although the processor 20 could execute other types of programmed instructions.

The memory 22 stores these programmed instructions for one or more aspects of the present invention as described herein, including the method for diagnosing whether a subject has a condition, although some or all of the programmed instructions could be stored and/or executed elsewhere. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor 20, can be used for the memory 22.

The display 24 is used to show data and information to the operator, such as the diagnosed Alzheimer's disease state for a subject, although other types of data and information could be displayed. The display 24 comprises a computer display screen, such as a CRT or LCD screen by way of example only, although other types and numbers of displays could be used.

The user input device 26 is used to input selections, such as information about a subject or proteins found in one or more cerebrospinal fluid samples from a subject, although other types of data could be input. The user input device 26 comprises a computer keyboard and a computer mouse, although other types and numbers of user input devices 26 can be used.

The input/output interface system 28 is used to operatively couple and communicate between the diagnostic processing system 12, the database server system 14, and the database compilation processing system 16 via communications network 18, although other types and numbers of connections and other configurations could be used. In this particular embodiment, the communication network 18 is the Internet and uses industry-standard protocols including SOAP, XML, LDAP, and SNMP, although other types and numbers of communication systems, such as a direct connection, a local area network, a wide area network, modems and phone lines, e-mails, and/or wireless communication technology each having their own communications protocols, could be used.

The database server system 14 stores information relating to proteins associated and not associated with Alzheimer's disease and processes and handles requests for the information, although the database server system 14 can store other types of information and the information relating to protein expression levels associated and not associated with Alzheimer's disease can be stored at other locations, such as in the memory 22 in the diagnostic processing system 12. The database server system 14 also includes a central processing unit (CPU) or processor, a memory, and an input/output interface system which are coupled together by a bus or other link, although other numbers and types of components and systems in other configurations can be used. The processor in the database server system 14 shown in FIG. 1 executes a program of stored instructions for one or more aspects of the present invention as described herein, including processing and handling requests for the information relating to proteins associated and not associated with Alzheimer's disease. The memory stores these programmed instructions for one or more aspects of the present invention as described herein, although some or all of the programmed instructions could be stored and/or executed elsewhere, such as in one or memories of provider systems. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor, can be used for the memory in the database server system 14. The input/output interface system in the database server system 14 is used to operatively couple and communicate between the database server system and the diagnostic processing system 12 and the database compilation processing system 16, although other types of connections could be used.

The database compilation processing system 16 can obtain proteomes of cerebrospinal fluid samples collected from subjects diagnosed with Alzheimer's disease, can obtain proteomes of cerebrospinal fluid samples collected from subjects diagnosed as not having the Alzheimer's disease state, compares the samples from the subjects with the disease to the samples from the subject without the disease, characterizes the samples and generating data based on the characterization, and analyzes the data to identify one or more proteins useful in assisting in the diagnosis of the Alzheimer's disease state to generate the database, although the database compilation processing system 16 can perform other types and numbers of functions and provide other types of outputs and can be embodied in other numbers of systems. The database compilation processing system 16 a central processing unit (CPU) or processor 32, a memory 34, a display 36, user input device 38, and an input/output interface system 39 are coupled together by a bus or other link 40, although the database compilation processing system 16 can comprise other numbers and types of components and systems in other configurations. The processor 32 executes a program of stored instructions for one or more aspects of the present invention as described and illustrated herein, including the method for obtaining proteomes of cerebrospinal fluid samples collected from subjects diagnosed with the Alzheimer's disease state, obtaining proteomes of cerebrospinal fluid samples collected from subjects diagnosed as not having the Alzheimer's disease state, comparing the samples from the subjects with the disease to the samples from the subject without the disease, characterizing the samples and generating quantitative data based on the characterization, and analyzing the quantitative data to identify one or more proteins useful in assisting in the diagnosis of the Alzheimer's disease state to generate the database, although the processor 32 could execute other types of programmed instructions.

The memory 34 stores these programmed instructions for one or more aspects of the present invention as described herein, including the method for diagnosing a subject's Alzheimer's disease state, although some or all of the programmed instructions could be stored and/or executed elsewhere. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor 32, can be used for the memory 34.

The display 36 is used to show data and information to the operator, such as the stored database, although other types of data and information could be displayed. The display 36 comprises a computer display screen, such as a CRT or LCD screen by way of example only; other types and numbers of displays could be used.

The user input device 38 is used to input selections, such as information about proteomes of cerebrospinal fluid samples collected from subjects diagnosed with Alzheimer's disease and proteomes of cerebrospinal fluid samples collected from subjects diagnosed as not having Alzheimer's disease; other types of data could be input. The user input device 38 comprises a computer keyboard and a computer mouse, although other types and numbers of user input devices 38 can be used.

The input/output interface system 39 is used to operatively couple and communicate between the database compilation processing system 16 and the diagnostic processing system 12 and the database server system 14 via the communications network 18. Other types and numbers of connections and other configurations could be used.

Although an example of embodiments of the diagnostic processing system 12, the database server system 14, and the database compilation processing system 16 is described and illustrated herein, each of the diagnostic processing system 12, the database server system 14, and the database compilation processing system 16 of the present invention could be implemented on any suitable computer system or computing device. It is to be understood that the devices and systems of the exemplary embodiments are for exemplary purposes, as many variations of the specific hardware and software used to implement the exemplary embodiments are possible, as will be appreciated by those skilled in the relevant art(s).

Furthermore, each of the systems of the present invention may be conveniently implemented using one or more general purpose computer systems, microprocessors, digital signal processors, micro-controllers, and the like, programmed according to the teachings of the present invention as described and illustrated herein, as will be appreciated by those skilled in the computer and software arts.

In addition, two or more computing systems or devices can be substituted for any one of the systems in any embodiment of the present invention. Accordingly, principles and advantages of distributed processing, such as redundancy, replication, and the like, also can be implemented, as desired, to increase the robustness and performance the devices and systems of the exemplary embodiments. The present invention may also be implemented on computer system or systems that extend across any network using any suitable interface mechanisms and communications technologies including, for example telecommunications in any suitable form (e.g., voice, modem, and the like), wireless communications media, wireless communications networks, cellular communications networks, G3 communications networks, Public Switched Telephone Network (PSTNs), Packet Data Networks (PDNs), the Internet, intranets, a combination thereof, and the like.

The present invention may also be embodied as a computer readable medium having instructions stored thereon for diagnostic processing as described herein, which when executed by a processor, cause the processor to carry out the steps necessary to implement the methods of the present invention.

EXAMPLES

The following examples are provided to illustrate embodiments of the present invention but are by no means intended to limit its scope.

Example 1

CSF Samples

Antemortem lumbar CSF samples from several CSF banks and other sites in the United States were shipped on dry ice and stored at −70° C. until needed. A total of 68 CSF samples were used, 34 from AD patients and 34 from non-AD patients. The samples from AD patients included 31 retrospective samples (AD diagnosis confirmed at post-mortem examination performed by contributing institutions) and 3 prospective samples (2 diagnosed as probable AD and 1 diagnosed as possible AD based on the NINCDS-ADRDA criteria (McKhann et al., "Clinical Diagnosis of Alzheimers-Disease—Report of the NINCDS-ADRDA Work Group Under the Auspices of Department of Health and Human Services Task Force on Alzheimers Disease," *Neurology* 34:939-944 (1984), which is hereby incorporated by reference in its entirety). The non-AD CSF included samples from control patients with no indication of dementia or neurodegenerative disease [normal (n=9), hydrocephalus (n=2), spinal schwannoma (n=1), head trauma (n=1)] and neurological controls [Parkinson's disease (n=0), multiple sclerosis (n=3), neurosyphilis (n=3), Pick's disease (n=2), dementia with Lewy bodies (n=1), Huntington's disease (n=1), primary progressive aphasia (n=1)]. These CSF samples were visually inspected and appeared to be free of blood contamination. Also, the protein spot changes identified by You et al. (You et al., "The Impact of Blood Contamination on the Proteome of Cerebrospinal Fluid," *Proteomics* 5:290-296 (2005), which is hereby incorporated by reference in its entirety) to be indicative of blood contamination were not present on the CSF 2DE gels.

Example 2

Two-Dimensional Gel Electrophoresis

The details of the protocols used for performing two-dimensional gel electrophoresis (2DE) have been previously published (Hatzimanikatis et al., "Proteomics: Theoretical and Experimental Considerations," *Biotechnol Prog* 15:312-318 (1999), which is hereby incorporated by reference in its entirety). Briefly, 250 μL of CSF (containing approximately 100 μg of protein) were precipitated using ice-cold ethanol. The resulting protein pellet was dissolved in a solution of 9 M urea (Bio-Rad), 2% 2-mercaptoethanol (J. T. Baker), 2% IGEPAL (Sigma), and 0.25% carrier ampliolytes (Bio-Rad). The sample was then hydrated directly into 18 cm, 3-10 nonlinear immobilized pH gradient (IPG) isoelectric focusing gels (Amersham Biosciences). Isoelectric focusing was then performed at 20° C. using the Protean IEF unit (Bio-Rad Laboratories) for a total of 100 kVh to separate proteins in the first dimension by isoelectric point. The IPG gels were equilibrated in solutions containing dithiothreitol (Bio-Rad) and subsequently iodoacetamide (Fluka) for reduction and alkylation of the focused proteins. Polyacrylamide gel electrophoresis was performed using 12-15% T vertical gradient slab gels to separate proteins in the second dimension by protein size. The separated proteins were fixed, stained with SYPRO Ruby Protein Gel Stain (Molecular Probes), and destained for 24 hours in a solution of 10% methanol and 7% acetic acid. The gels were scanned on a FLA-3000 Fluorescent Image Analyzer (Fuji Photo Film Company).

The resulting gel images were imported into the Melanie software package (Version 4.0, GeneBio). Spots were auto-detected by the software and the detected spots were manually edited to remove technical artifacts. For consistency, a single person edited the same region on all gels. A master gel image was created by combining the spots present in gels from three normal samples, two AD samples, one Parkinson's disease sample, one hydrocephalus sample, and one Huntington's disease sample. The master gel image contains all of the spots from these eight 2DE gels and acts as a reference for the sample gels. CSF gels from both AD and non-AD patients were used to create the master gel to account for the fact that there may be spots that only appeared in CSF gels from one of these patient groups. The spots from each of the 68 sample gels were then matched to the master gel, which allowed an inter-gel spot comparison. Matching was initially performed using the automatic matching function in the Melanie software and was then manually edited by a single individual to correct for obvious missed or incorrect matches. The percent integrated optical density (% volume) of each 2DE spot in each gel was then exported to a spreadsheet file. The % volume represents the relative amount of a given protein in the CSF sample. If a spot was not detected on a gel, it was assigned zero % volume for subsequent statistical analysis.

Example 3

Statistical Analysis

The % volume data were analyzed using the RF method described elsewhere (Hampel et al., "Discriminant Power of Combined Cerebrospinal Fluid Tau Protein and of the Soluble Interleukin-6 Receptor Complex in the Diagnosis of Alzheimer's Disease," *Brain Res* 823:104-112 (1999); Choe et al., "Studies of Potential Cerebrospinal Fluid Molecular Markers for Alzheimer's Disease," *Electrophoresis* 23:2247-2251 (2002); Lescuyer et al., "Identification of Post-Mortem Cerebrospinal Fluid Proteins as Potential Biomarkers of Ischemia and Neurodegeneration," *Proteomics* 4:2234-2241 (2004), which are hereby incorporated by reference in their entirety). Briefly, N classification trees are built with each tree using an independent subset (approximately two-thirds) of the samples. To build a tree, the program chooses a random subset of m variables at each node and determines which variable in the subset can best separate the classes (e.g. AD gels and non-AD gels). After a tree is constructed, the program runs the remaining one-third of samples (termed the out-of-bag samples) down the classification tree and predicts what class each sample belongs to based on the % volume data. To determine the overall predicted class for a sample, each tree gives one vote for the class it determines the sample to belong to, and the votes are tallied over all N trees. For each sample, the class that gets the most votes is the predicted class for that sample. The predicted class for the out-of-bag samples is then compared to the actual class and the out-of-bag error (oob error) is calculated. This error is a statistical prediction of the ability of the forest to classify future data sets. It has been shown that the predicted error using this method is unbiased and equivalent to using one-half of the samples as a training set and one-half of the samples as a validation set (Breiman L., "Random Forests," *Machine Learning* 45:5-32 (2001), which is hereby incorporated by reference in its entirety). After the oob error is calculated, the value of each variable is then individually modified (e.g. the % volume measurement for a specific spot is changed) and the modified samples are re-classified on the existing forest. Based on the magnitude of the change in the oob error after modification, the importance of that particular variable in classifying the samples can be determined. To visualize the classification, a plot of canonical functions indicating the scaled distances between samples can be constructed. The functions are calculated using the proximity of each possible pair of samples. The proximity of the two samples is based on the number of times the two samples are placed in the same terminal node of a classification tree.

In this study, the initial variable list consisted of all of the spots present on the 2DE gels. The value of m (the number of variables in the random subsets) that minimized the oob error was then determined and subsequently used to create a forest of 2000 trees. The 100 variables determined by this forest to have the highest importance in classifying samples were then used to build another forest. The 50 variables with the highest importance from this forest were then used to build another forest and the process was repeated until additional removal of variables increased the oob error. As controls, RF analyses were also performed on data sets where a randomly selected subset of protein spots was used and where half of the samples were labeled with a reversed diagnosis (i.e. in the input files for the RF program half of AD samples were labeled as non-AD and vice versa).

Diagnostic accuracy was assessed by using a receiver operating characteristic (ROC) analysis. Two forms of this analysis were performed. The first form follows the suggestions of Raubertas et al. (Raubertas et al., "ROC Curves for Classification Trees," *Med Decis Mak* 14:169-174 (1994), which is hereby incorporated by reference in its entirety) for creating an ROC-like curve for a diagnosis based on classification trees. In this type of analysis the sensitivity-specificity combinations are determined by changing the misclassification cost ratio (the cost of a false-negative diagnosis/the cost of a false-positive diagnosis). The RF analysis uses the cost ratio to determine how to split the samples into the AD and non-AD groups at each node of the tree. The default value for the cost ratio is 1 and for this analysis the cost ratio was varied between 0.2 and 5. Because the RF analysis uses a large number of classification trees (rather than a single tree as was the focus of (Raubertas et al., "ROC Curves for Classification Trees," *Med Decis Mak* 14:169-174 (1994), which is hereby incorporated by reference in its entirety)) there is another way an ROC analysis could be performed. In the standard RF analysis with two classes (AD and non-AD), a sample is classified as being in the AD class if over 50% of the classification trees vote for the AD class. An ROC analysis was therefore performed by varying the threshold percentage of votes needed to classify a sample as belonging to the AD class between 20% and 80%. The area under the curve was calculated using the trapezoidal method.

Example 4

Protein Identification

Some of the proteins in 2DE spots of interest were identified using a previously published 2DE CSF map (Finehout et al., "Towards Two-Dimensional Electrophoresis Mapping of the Cerebrospinal Fluid Proteome From a Single Individual," *Electrophoresis* 25:2564-2575 (2004), which is hereby incorporated by reference in its entirety). The remaining spots were identified using tryptic digestion followed by tandem mass spectrometry (4700 Proteomics Analyzer, Applied Biosystems) using previously published methods (Finehout et al., "Comparison of Automated In-Gel Digest Methods for Femtomole Level Samples," *Electrophoresis* 24:3508-3516 (2003), which is hereby incorporated by reference in its entirety). Peptide mass fingerprint data were collected in positive reflector mode in the range of 900 to 4000 mass to charge ratio (m/z). Several of the highest intensity non-trypsin peaks were then selected for tandem mass spectrometry (MS/MS) analysis. The selected peptides were isolated and then fragmented using air, at 1E-6 torr, as the collision gas. The spectra were analyzed using GPS Explorer (Version 2.0, Applied Biosystems), which acts as an interface between the Oracle database containing raw spectra and a local copy of the Mascot search engine (Version 1.8, (Perkins et al., "Probability-Based Protein Identification by Searching Sequence Databases Using Mass Spectrometry Data," *Electrophoresis* 20:3551-3567 (1999), which is hereby incorporated by reference in its entirety)). The spectral data were searched against a locally stored copy of the NCBInr human protein sequence database using the Mascot search engine. A mass tolerance of 25 ppm was used for the peptide mass fingerprint data and of 0.2 Da for the tandem mass spectrometry data. For a match to be considered a valid identification, a confidence interval (% CI) calculated by Applied Biosystems GPS Explorer (GPS), of at least 95% was required. The GPS % CI is calculated from the Mascot Mowse score with the significance threshold removed and a 95% CI corresponds to p<0.05. The GPS % CI is calculated from the mascot mouse score with the significance threshold removed and the closer the % CI is to 100%, the higher the probability that the identification is correct.

The CSF 2DE gels had an average of 1188 detected spots. The master image, created in silico by combining the spots from eight gel images, had a total of 1938 spots. A Students t-test analysis comparing the % volume of 2DE spots in AD and non-AD gels identified 252 spots with a significant change in expression level (p<0.05), 79 of which had a p<0.01.

An initial RF analysis was performed using the % volume data for all 1938 matched spots on all 68 gels. This initial forest was able to correctly classify 26 of 34 AD samples and 26 of 34 non-AD samples and the oob error rate was 23.5%. As a control, the same set of spots with half of the disease classifications reversed was then used to build another forest. This second forest correctly classified only 15 of the AD gels and 13 of the non-AD gels with an oob error rate of 58.8%.

Protein spots determined by RF to be less statistically important were then removed. Ultimately, a panel of 23 protein spots was found that could be used in RF to correctly classify 32 of 34 AD samples and 32 of 34 non-AD samples with an oob error rate of 5.9%. As a control, a set of 23 random spots were used in an RF analysis and resulted in a classification tree forest with an oob error rate of 42.7%.

Figure 2:
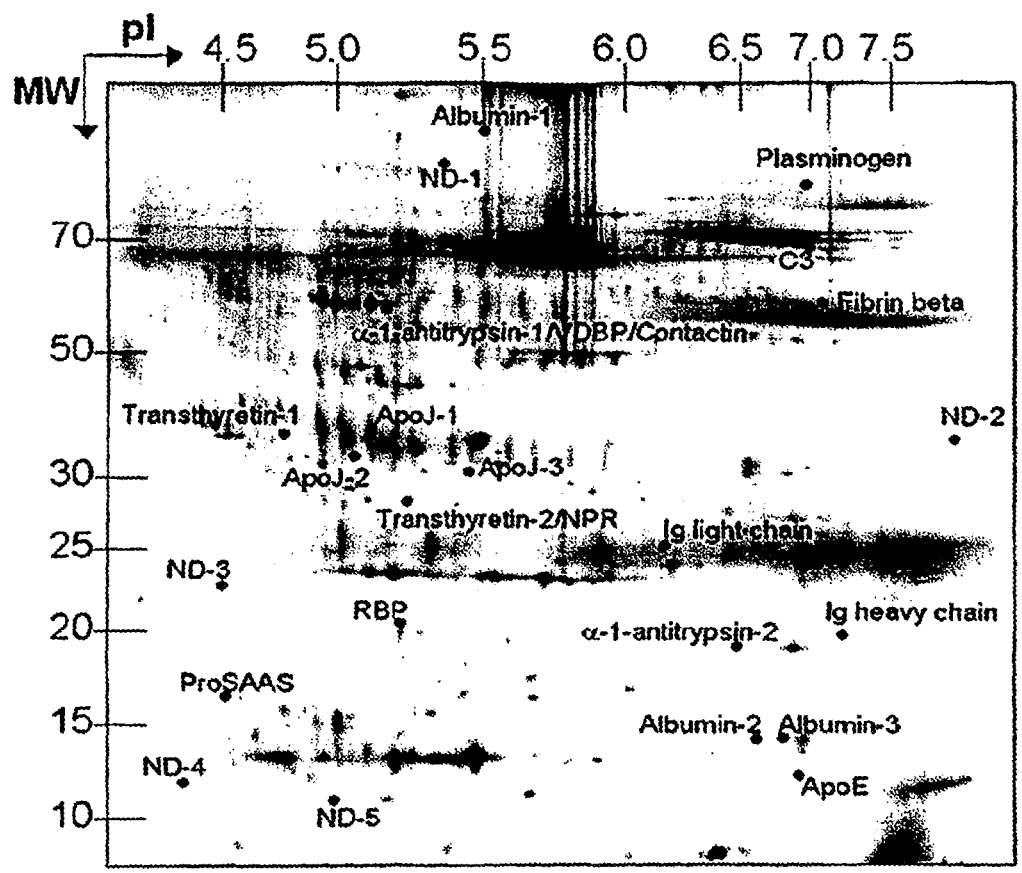
FIG. 2 shows the image of a CSF 2DE gel from a normal subject. The proteins are separated by isoelectric point (pI) in the horizontal direction and molecular weight (approximate MW shown in kDa) in the vertical direction. The 23 spots found to be useful in differentiating AD from nonAD samples are labeled with the protein identified in the spot. If more than one isoform of a protein was identified, the protein name is followed by a dash and an isoform number. ApoE=Apolipoprotein E, ApoJ=Apolipoprotein J, C3=Complement component 3, RBP=Retinol binding protein, NPR=Neuronal pentraxin receptor, VDBP=Vitamin D-binding protein, and ND=No identification.

The locations of the 23 spots (identified using the RF analysis) are indicated in FIG. 2 and the protein identification information and NCBInr accession numbers are shown in Table 1. Table 1 also lists the amino acid sequence coverage of the peptides detected in the MS spectra for each spot. Two of the spots were found to contain more than one protein. The effects of the multiple proteins on the % volume cannot be deconvoluted, and therefore it is not possible to determine which of the proteins is responsible for the difference between the AD and non-AD samples. All identified proteins are therefore included in the discussion.

Figure 3:
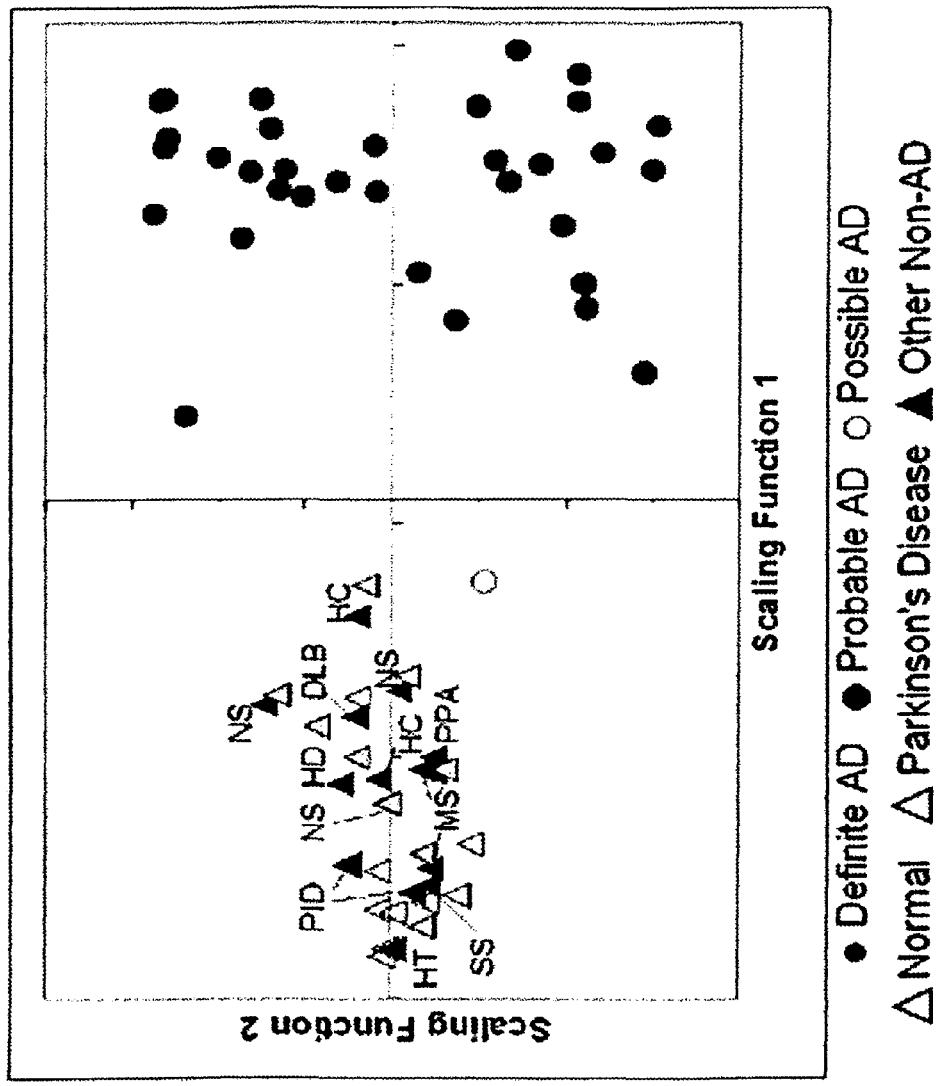
FIG. 3 illustrates the scatter plot showing scaled distances among the 68 CSF samples based on RF classifications using the 23 identified protein spots. The diagnosis for each sample is also shown. DLB-Dementia with Lewy Bodies, HC-Hydrocephalus, HD-Huntington's Disease, HT-Head Trauma, MS-Multiple Sclerosis, NS-Neurosyphilis, PID-Pick's Disease, PPA-Primary Progressive Aphasia, and SS-Spinal Schwannoma.
Figure 4A:
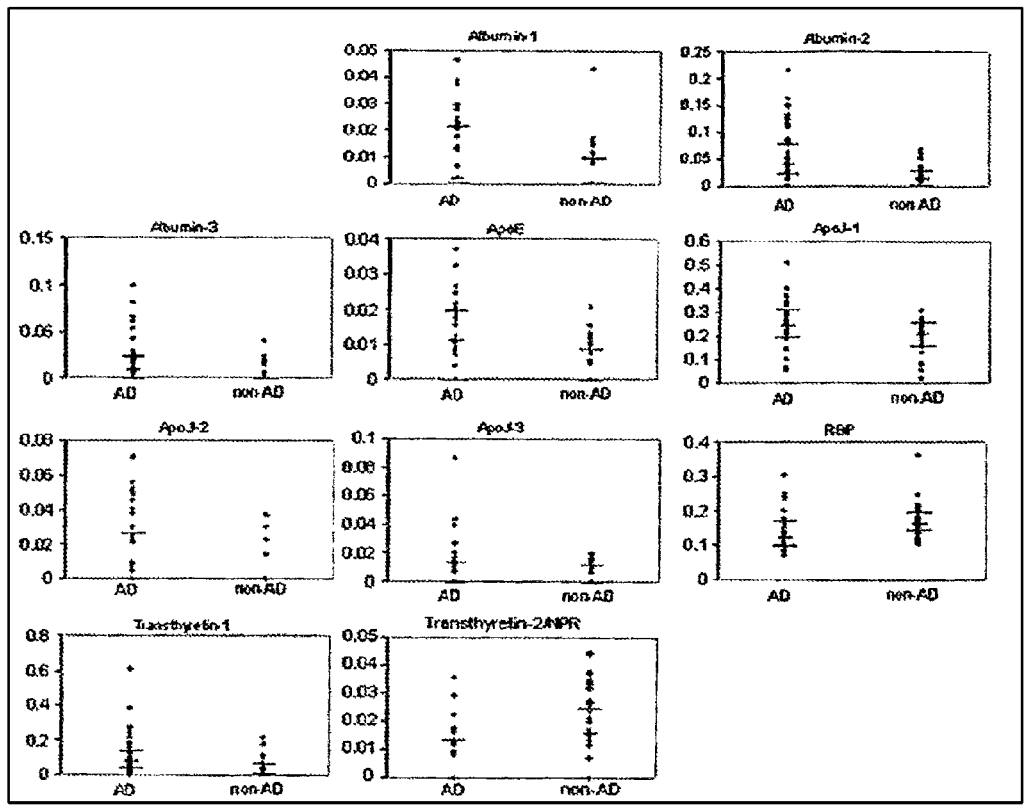
FIG. 4A-D illustrates plots showing the distribution of % volumes for each of the 23 spots in AD and non-AD gels. Lines indicate the median, as well as $25^{th}$ and $75^{th}$ quartiles.
Figure 4B:
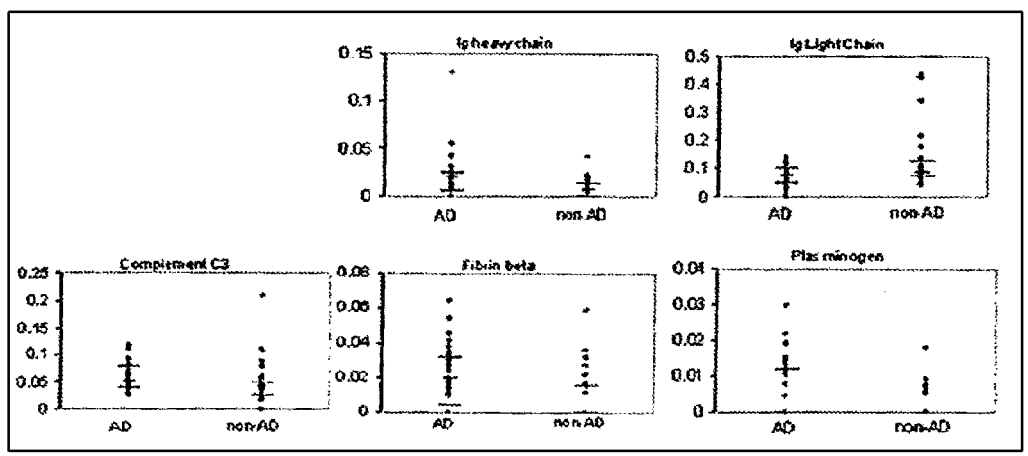
Figure 4C:
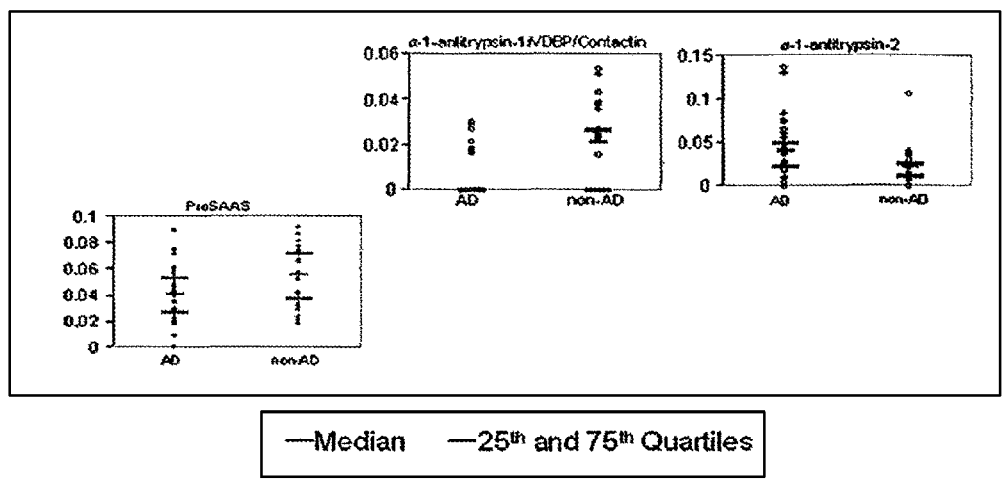
Figure 4D:
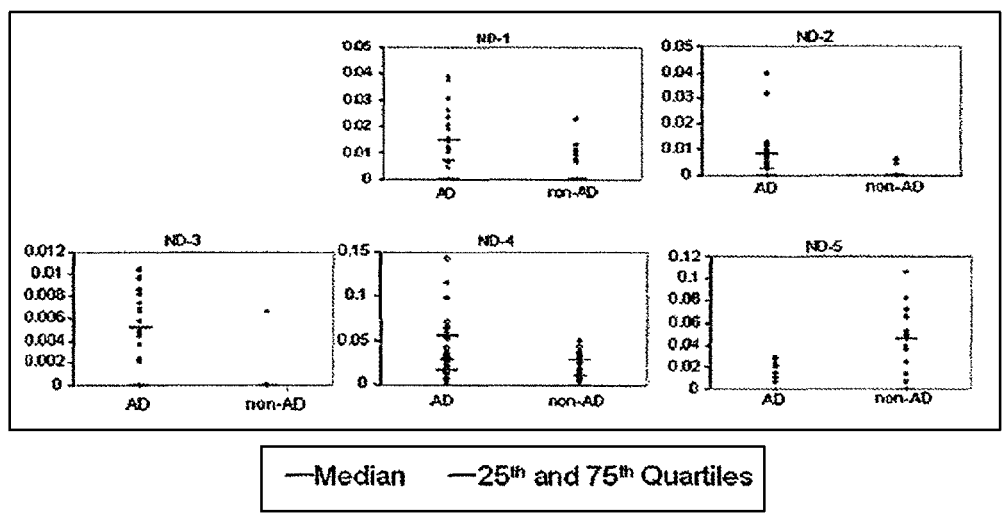

FIG. 3, a plot of the scaled distances between each of the CSF samples, reflects the ability of the panel of 23 spots to separate AD from non-AD gels. The misclassified AD samples include one possible AD and one definite AD sample. The misclassified non-AD samples include one sample from a normal patient and one sample from a hydrocephalus patient. FIG. 4 shows the % volume distribution for each of the 23 marked spots in the AD and non-AD gels. It should be noted that although no significant increase or decrease may exist for some proteins (based on a univariate analysis) the data for the 23 proteins taken together (using a multivariate analysis) was used to successfully classify AD and non-AD samples.

Figure 5:
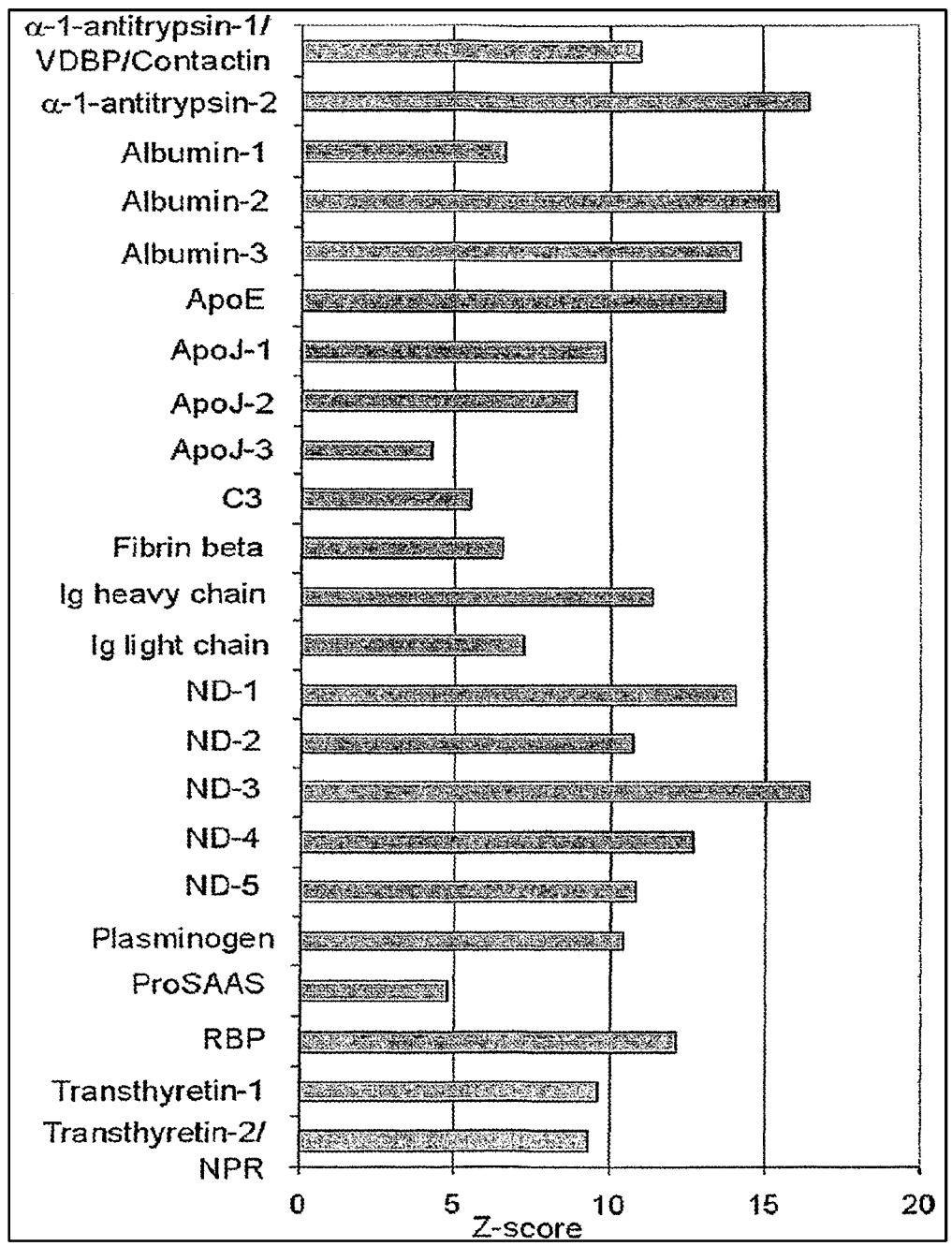
FIG. 5 shows the z-scores for each of the 23 spots used to classify the 2DE gels. The z-score is equal to the raw importance score divided by the standard deviation; a higher score indicates a greater importance in gel classification.
Figure 6A:
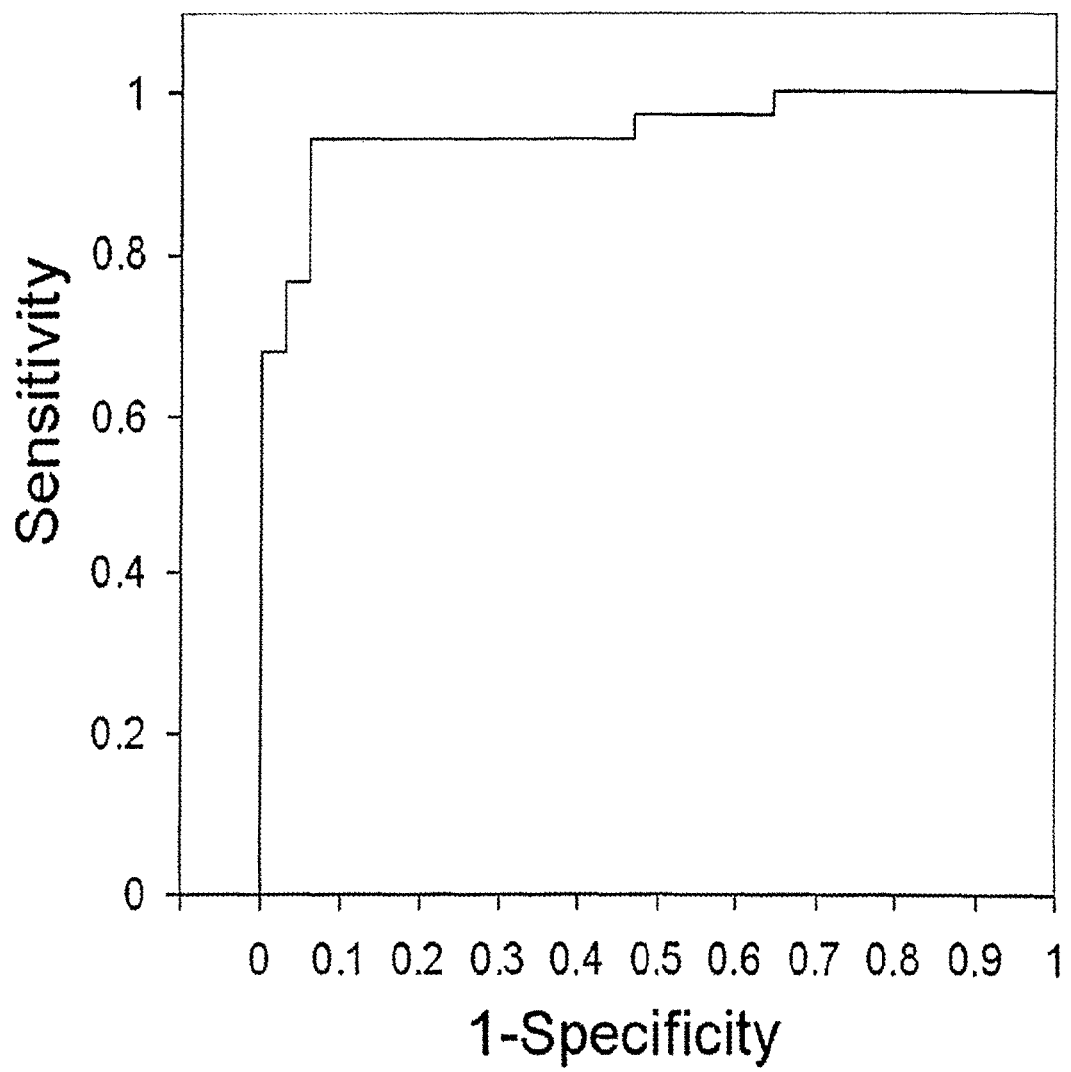
FIG. 6A-B shows results of the ROC analyses.
Figure 6B:
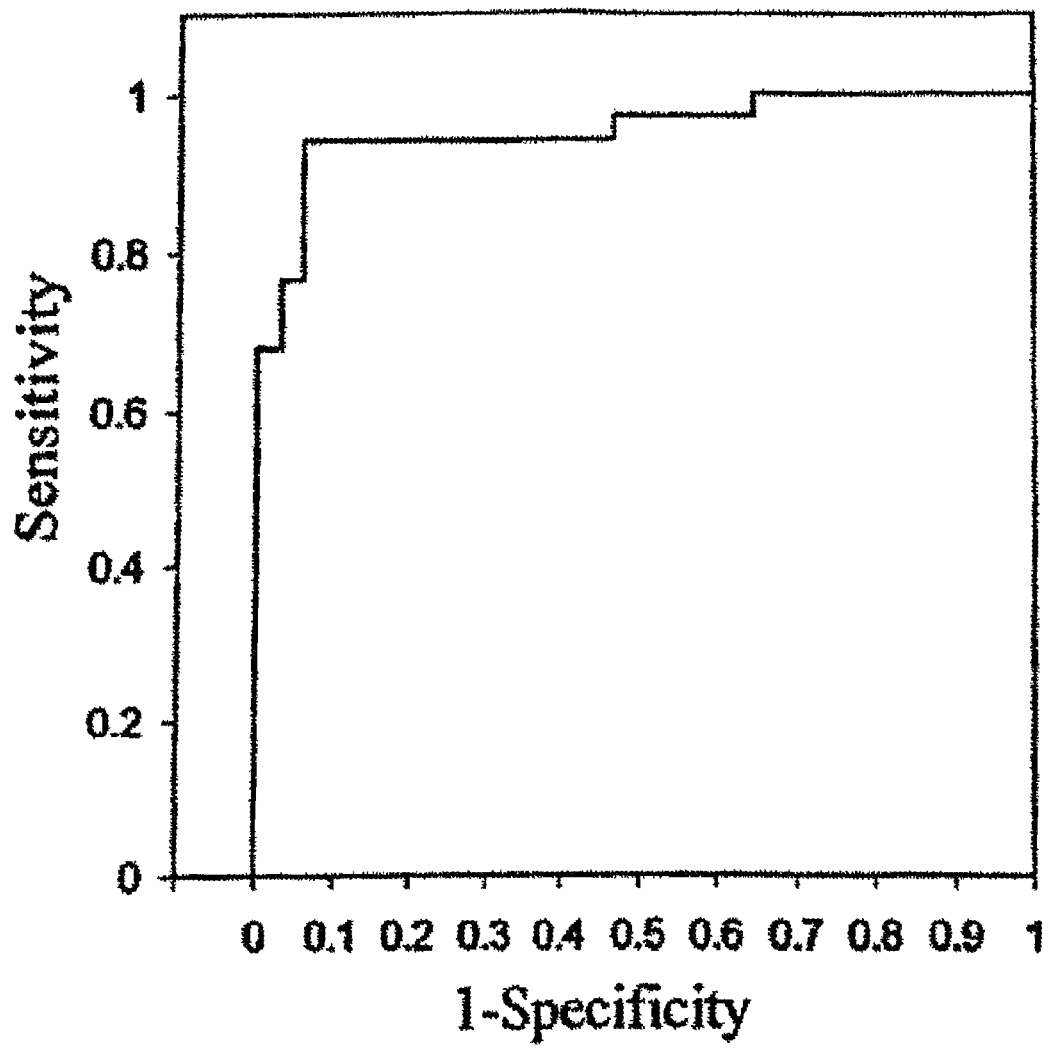

The relative importance of each of the 23 spots in classifying the 2DE gels, as indicated by the z-score, is shown in FIG. 5. The z-score is defined as the raw importance score divided by the standard deviation; the higher the z-score the greater the importance of the spot. The α-1-antitrypsin-2 isoform has the highest z-score (16.5) and the ApoJ-3 isoform has the lowest (4.2). The results of the ROC analyses are shown in FIG. 6. FIG. 6A shows the curve that results from the method suggested in (Raubertas et al., "ROC Curves for Classification Trees," *Med Decis Mak* 14:169-174 (1994), which is hereby incorporated by reference in its entirety) for analyzing classification tree studies. Although this is not a true ROC curve (no diagnostic threshold is varied), it can be used to identify the best combinations of sensitivity and specificity for classification trees based on a set of predictor variables. The ROC curve in FIG. 6B is generated by varying the threshold percentage of classification tree votes needed to classify a sample as AD. The two curves show a similar shape and the area under the ROC curve in FIG. 6B is 0.96.

The proteins in several spots in Table 1 had not been identified in the previously published 2DE CSF map (Finehout et al., "Towards Two-Dimensional Electrophoresis Mapping of the Cerebrospinal Fluid Proteome From a Single Individual," *Electrophoresis* 25:2564-2575 (2004), which is hereby incorporated by reference in its entirety). These were analyzed using enzymatic digestion followed by tandem mass spectrometry. An example of the acquired spectra, both MS and MS/MS, is shown in FIG. 7. The MS/MS spectra include y-ions, b-ions, a-ions, immonium ions, and internal fragment ions.

TABLE 1

Summary of protein spots determined by RF to be useful in differentiating AD gels from non-AD gels.

| Spot | Accession # | pI | MW (kDa) | Mowse score | % CI | MS sequence coverage |
|---|---|---|---|---|---|---|
| Albumin-1* | 178345 | 6.0 | 69.2 | 66 | 99.9 | 66-75, 89-97, 169-184, 348-372, 376-383, 397-413, 427-434, 438-452, 509-524, 570-581 |
| Albumin-2 | 178345 | 6.0 | 69.2 | 37 | 98 | 509-524, 570-581 |
| Albumin-3* | 178345 | 6.0 | 69.2 | 70 | 99.9 | 491-499, 509-543, 570-581 |
| α-1-Antitrypsin-1* | 1942629 | 5.4 | 44.3 | 86 | 100 | 11-39, 102-125, 137-155, 224-233, 260-282, 301-328, 344-380 |
| α-1-Antitrypsin-2 | 1942629 | 5.4 | 44.3 | 129 | 100 | 260-274, 291-300, 311-328, 344-365 |
| Apolipoprotein E* | 178853 | 5.8 | 36.2 | 62 | 99.6 | 177-185, 199-207, 210-224, 259-278 |
| Apolipoprotein J-1 | 178855 | 6.3 | 48.8 | 149 | 100 | 274-289, 293-303, 353-392 |
| Apolipoprotein J-2* | 178855 | 6.3 | 48.8 | 18 | 95 | 95-105, 135-161, 166-189, 376-392 |
| Apolipoprotein J-3* | 178855 | 6.3 | 48.8 | 56 | 98.7 | 12-21, 150-161, 166-189, 376-392 |
| Complement Component 3 | 4557385 | 6.0 | 18.7 | 182 | 100 | 36-66, 105-119, 137-148, 208-258, 264-281, 290-304, 323-359, 387-425, 428-478, 489-497, 509-544, 567-600, 634-657 |
| Contactin* | 414791 | 5.6 | 113.3 | 27 | 95 | 226-249, 643-653, 722-732 |
| Fibrin Beta | 223002 | 8.0 | 50.8 | 59 | 99.3 | 10-28, 81-108, 120-152, 310-323 |
| Ig Heavy Chain* | 10334595 | 8.1 | 39.0 | 218 | 97 | 260-285, 332-354 |
| Ig Light Chain | 21669417 | 6.2 | 28.7 | 152 | 100 | 82-101, 135-169, 177-210, 218-234 |
| Neuronal Pentraxin Receptor* | 17402890 | 5.8 | 52.7 | 68 | 98 | 204-213, 277-294, 301-307, 366-374, 478-487 |
| Plasminogen* | 190026 | 7.0 | 90.5 | 51 | 96.4 | 88-109, 137-153, 412-427, 446-453, 513-523, 635-664, 681-696 |
| ProSAAS | 7019519 | 6.2 | 27.4 | 146 | 100 | 62-104, 118-138, 202-216 |
| Retinol Binding Protein | 230284 | 5.27 | 21.0 | 99 | 100 | 30-58, 122-139 |
| Transthyretin-1* | 339685 | 5.5 | 15.9 | 254 | 100 | 12-25, 39-66, 71-93, 95-117 |

TABLE 1-continued

Summary of protein spots determined by RF to be useful in differentiating AD gels from non-AD gels.

| Spot | Accession # | pI | MW (kDa) | Mowse score | % CI | MS sequence coverage |
|---|---|---|---|---|---|---|
| Transthyretin-2* | 339685 | 5.5 | 15.9 | 128 | 100 | 12-24, 71-116 |
| Vitamin D-binding protein* | 72105 | 5.4 | 53.0 | 68 | 98 | 31-87, 128-149, 208-229, 342-363, 428-440 |

*Indicates spot was not identified in previous 2DE CSF map (Finehout et al., "Towards Two-Dimensional Electrophoresis Mapping of the Cerebrospinal Fluid Proteome From a Single Individual," Electrophoresis 25: 2564-2575 (2004), which is hereby incorporated by reference in its entirety).
The NCBInr accession number of the protein identified, as well as the theoretical pI and MW (calculated from the amino acid sequence of the intact protein), are shown. The Mascot Mowse score (Perkins et al., "Probability-based Protein Identification by Searching Sequence Databases Using Mass Spectrometry Data," Electrophoresis 20: 3551-3567 (1999), which is hereby incorporated by reference in its entirety), GPS % CI, and amino acid sequence coverage obtained using MS are also included.

When using all 1938 detected spots in the RF analysis, there was a large increase in error when the disease classifications for half of the samples were switched (AD sample labeled as non-AD and vice-versa). This is consistent with the idea that there is a spot pattern present on the gels that differentiates the AD and non-AD gels. In FIG. 4, it can be seen that the % volumes for some of the protein spots do not show a clear difference in distribution between the two classes. This may be due to the heterogeneity of the AD and especially the non-AD classes. The AD class contains samples from patients at different stages of the disease and the non-AD class contains patients with different types of neurological disorders. Because the RF method uses classification trees, these 2DE spots may be useful in separating AD gels from some, but not all, of the non-AD sample types. Also, given that a multivariate approach combines the information from multiple variables when classifying the samples, a combination of the % volume changes across the panel of 23 spots will have a greater statistical significance than the individual changes.

The proteins in 18 of the 23 marked spots have been identified and most of the identified proteins have a known relationship to AD pathology. For discussion, the identified proteins have been arranged into four categories. The first group consists of proteins related to the transport of β-amyloid (Aβ) and includes albumin, vitamin D-binding protein, transthyretin, retinol binding protein, apolipoprotein E (ApoE), and apolipoprotein J (ApoJ). The proteins in the second group are those involved in inflammation and the immune response and include immunoglobulins, plasminogen, fibrinogen beta, and complement component 3. Two inhibitors of proteolytic enzymes, α-1-antitrypsin and proSAAS, are the third group. The final group consists of two neuronal membrane proteins: contactin and neuronal pentraxin receptor.

Example 5

Aβ Transport

Three of the marked 2DE spots in FIG. 2 contain albumin. Albumin is the most abundant protein in CSF, constituting up to 80% of the protein content (Peters T., "All About Albumin: Biochemistry, Genetics, and Medical Applications," San Diego, Calif.: *Academic Press* (1996), which is hereby incorporated by reference in its entirety). Its main function is believed to be the stabilization of the physical environment of the blood, but it is also involved in other functions such as metabolite transport and lipid metabolism (Peters T., "All About Albumin Biochemistry, Genetics, and Medical Applications," San Diego, Calif.: *Academic Press* (1996), which is hereby incorporated by reference in its entirety). Studies have suggested that albumin interacts with Aβ in several ways: albumin has been found in senile plaques (Galeazzi et al., "Albumin Protects Human Red Blood Cells Against A Beta (25-35)-Induced Lysis More Effectively Than ApoE," *Neuroreport* 13:2149-2154 (2002), which is hereby incorporated by reference in its entirety); in vitro, albumin prevents the formation of Aβ macro-aggregates and protects red blood cells from lysis by $A\beta_{25-35}$ (Galeazzi et al., "Albumin Protects Human Red Blood Cells Against A Beta(25-35)-Induced Lysis More Effectively Than ApoE," *Neuroreport* 13:2149-2154 (2002), which is hereby incorporated by reference in its entirety); and evidence indicates that in plasma the majority of Aβ (~89%) is bound to albumin (Biere et al., "Amyloid Beta-Peptide is Transported On Lipoproteins and Albumin in Human Plasma," *J Biol Chem* 271:32916-32922 (1996), which is hereby incorporated by reference in its entirety). All three albumin spots showed an increase in % volume in AD patients. Based on the molecular weights, the albumin-1 spot contains intact albumin while the albumin-2 and albumin-3 spots contain an albumin fragment. The mass spectra for albumin-2 and albumin-3 include peaks corresponding to amino acids 491 to 581, indicating that the spots contain C-terminal fragments of albumin. This data suggests that albumin processing may be altered in AD versus non-AD CSF. A previous proteomic study also found an isoform of intact albumin that was decreased in the CSF of AD patients (Puchades et al., "Proteomic Studies of Potential Cerebrospinal Fluid Protein Markers for Alzheimer's Disease," *Brain Res Mol Brain Res* 118:140-146 (2003), which is hereby incorporated by reference in its entirety). Although studies have previously measured the total albumin content of CSF from AD and non-AD patients, no study has yet examined the utility of specific albumin fragments to monitor CNS health.

Vitamin D-binding protein, found in one of the spots with multiple proteins, is a member of the albumin family. It binds to and transports vitamin D and its metabolites (Peters T., "All About Albumin: Biochemistry, Genetics, and Medical Applications," San Diego, Calif.: *Academic Press* (1996), which is hereby incorporated by reference in its entirety). From the approximate molecular weight of the spot and the amino acid sequence coverage, the spot appears to contain intact vitamin D-binding protein. There is no previous study linking this protein to AD or dementia. This spot, which was also found to contain a-1-antitrypsin and contactin, showed a decrease in the % volume of the spot in AD patients.

Two of the marked spots in FIG. 2 contain transthyretin, which plays an important role in the transport of retinol (vitamin A) and thyroxine. Although plasma transthyretin is synthesized in the liver, studies have suggested that CSF transthyretin is synthesized in the choroid plexus (Herbert et al., "Transthyretin—A Choroid Plexus-Specific Transport Protein in Human-Brain," *Neurology* 36:900-911 (1986), which is hereby incorporated by reference in its entirety). In vitro experiments have shown transthyretin to form stable complexes with Aβ peptides in CSF and to inhibit Aβ aggregation (Schwarzman et al., "Transthyretin Sequesters Amyloid-Beta Protein and Prevents Amyloid Formation," *Proc Natl Acad Sci USA* 91:8368-8372 (1994), which is hereby incorporated by reference in its entirety). Transthyretin is present as a homotetramer in vivo with each monomer having a molecular weight of 15.9 kDa. The MW position of transthyretin-1 and transthyretin-2 suggest that they both may contain transthyretin dimers. The MS and MS/MS spectra and the amino acid sequence coverage for transthyretin-1 are shown in FIG. 6. Here, transthyretin-1 was found to display a higher average % volume and transthyretin-2 a lower % volume in the 2DE gels from AD patients. Others have found that the total transthyretin concentration (Serot et al., "Aging and Late Onset Alzheimer's Disease," *J Neurol Neurosurg Psychiatry* 63:506-508 (1997), which is hereby incorporated by reference in its entirety) and that of specific transthyretin isoforms (Davidsson et al., "Proteome Analysis of Cerebrospinal Fluid Proteins in Alzheimer Patients," *Neuroreport* 13:611-615 (2002); Puchades et al., "Proteomic Studies of Potential Cerebrospinal Fluid Protein Markers for Alzheimer's Disease," *Brain Res Mol Brain Res* 118:140-146 (2003), which are hereby incorporated by reference in their entirety) may be lowered in AD CSF.

Retinol-binding protein, which forms a complex with transthyretin and acts as an intracellular transporter of retinol (Zanotti et al., "Plasma Retinol-Binding Protein Structure and Interactions with Retinol, Retinoids, and Transthyretin," *Vitamins and Hormones—Advances in Research and Applications* 69:271-295 (2004), which is hereby incorporated by reference in its entirety), was identified in one of the marked spots at a molecular weight of approximately 21 kDa. Using an immunoassay on brain tissue, retinol-binding protein has been found to be enriched in the extracts from AD brain tissue compared to normal brain tissue (Maury et al., "Immunodetection of Protein-Composition in Cerebral Amyloid Extracts in Alzheimers-Disease—Enrichment of Retinol-Binding Protein," *J Neurol Sci* 80:221-228 (1987), which is hereby incorporated by reference in its entirety). The retinol-binding protein spot showed a similar % volume distribution in AD and non-AD patients, although the average value is slightly lower in AD patients. Previous proteomic studies have reported both statistically higher (Davidsson et al., "Proteome Analysis of Cerebrospinal Fluid Proteins in Alzheimer Patients," *Neuroreport* 13:611-615 (2002), which is hereby incorporated by reference in its entirety) and lower (Puchades et al., "Proteomic Studies of Potential Cerebrospinal Fluid Protein Markers for Alzheimer's Disease," *Brain Res Mol Brain Res* 118:140-146 (2003), which is hereby incorporated by reference in its entirety) concentrations of retinol-binding protein in the CSF of AD patients.

ApoE and ApoJ are the main lipoprotein carriers for Aβ, and both have been found in Aβ deposits in the brains of AD patients (DeMattos et al., "ApoE and Clusterin Cooperatively Suppress A Beta Levels and Deposition: Evidence that ApoE Regulates Extracellular A Beta Metabolism In Vivo," *Neuron* 41:193-202 (2004), which is hereby incorporated by reference in its entirety). Using a mouse model for AD, ApoJ and ApoE were found to cooperatively suppress Aβ levels and deposition (DeMattos et al., "ApoE and Clusterin Cooperatively Suppress A Beta Levels and Deposition: Evidence that ApoE Regulates Extracellular A Beta Metabolism In Vivo," *Neuron* 41:193-202 (2004), which is hereby incorporated by reference in its entirety). The brain is a major site of ApoE expression and the high level of sialylation indicates the ApoE in CSF originates in the brain rather than the plasma (Danik et al., "Clusterin and Apolipoprotein E Gene Expression in the Adult Brain," Finch C E, ed. *Clusterin in Normal Brain Functions and During Neurodegeneration*. Austin, Tex.: R. G. Landes Co. 17-34 (1999), which is hereby incorporated by reference in its entirety). ApoE has been found in the neurofibrillary tangles of AD (Zlokovic et al., "Nurovascular Interactions of Alzheimer's Amyloid Beta Peptide with Apolipoproteins J and E," Finch C E, ed. *Clusterin in Normal Brain Functions and During Neurodegeneration*. Austin, Tex.: R. G. Landes Co. 71-88 (1999), which is hereby incorporated by reference in its entirety) and may have a role in regulating the extracellular metabolism of Aβ in the CNS (DeMattos et al., "ApoE and Clusterin Cooperatively Suppress A Beta Levels and Deposition: Evidence that ApoE Regulates Extracellular A Beta Metabolism In Vivo," *Neuron* 41:193-202 (2004), which is hereby incorporated by reference in its entirety). Further, the ApoE4 allele is a genetic risk factor for AD (Saunders et al., "Apolipoprotein-E-Epsilon-4 Allele Distributions in Late-Onset Alzheimers-Disease and in Other Amyloid-Forming Diseases," *Lancet* 342:710-711 (1993), which is hereby incorporated by reference in its entirety), suggesting ApoE plays a role in the pathogenesis of AD. Previous proteomic studies have reported a decrease in intact ApoE isoforms in AD patients (Davidsson et al., "Proteome Analysis of Cerebrospinal Fluid Proteins in Alzheimer Patients," *Neuroreport* 13:611-615 (2002); Puchades et al., "Proteomic Studies of Potential Cerebrospinal Fluid Protein Markers for Alzheimer's Disease," *Brain Res Mol Brain Res* 118:140-146 (2003), which are hereby incorporated by reference in their entirety). The ApoE spot in FIG. 1 showed an increase in average % volume in AD patients. Based on the molecular weight, the spot contains a fragment of ApoE; the peptides detected in the mass spectra include amino acids 177 to 278, indicating that the peptide was truncated at the amino terminus. The pI of the ApoE spot is also closer to that of a C-terminal fragment starting at amino acid 177 (predicted pI=6.9) than the pI of full ApoE (predicted pI=5.8). It has been reported that the major form of ApoE associated with senile plaques is also truncated at the amino terminus (McGeer et al., "Apolipoprotein E and Apolipoprotein J (Clusterin) in the Brain in Alzheimer's Disease," Finch C E, ed. *Clusterin in Normal Brain Functions and During Neurodegeneration*. Austin, Tex.: R. G. Landes Co. 89-98 (1999), which is hereby incorporated by reference in its entirety).

Three of the identified spots in FIG. 2 contain ApoJ. Others have suggested that while plasma ApoJ originates in the liver, ApoJ of the CSF may also be synthesized in the glial cells of the brain (Choimiura et al., "Sp-40,40 is a Constituent of Alzheimers Amyloid," *Acta Neuropathol* 83:260-264 (1992), which is hereby incorporated by reference in its entirety). ApoJ is a major carrier of soluble Aβ in both the CSF and the plasma (Danik et al., "Clusterin and Apolipoprotein E Gene Expression in the Adult Brain," Finch C E, ed. *Clusterin in Normal Brain Functions and During Neurodegeneration*. Austin, Tex.: R. G. Landes Co. 17-34 (1999), which is hereby incorporated by reference in its entirety) and $A\beta_{1-40}$ bound to ApoJ was found to have a significant blood-brain barrier permeability and uptake in the choroid plexus (Zlokovic et al., "Neurovascular Interactions of Alzheimer's Amyloid Beta Peptide with Apolipoproteins J and E," Finch C E, ed. *Clusterin in Normal Brain Functions and During Neurodegeneration*. Austin, Tex.: R. G. Landes Co. 71-88 (1999), which is hereby incorporated by reference in its entirety). ApoJ attenuates Aβ neurotoxicity in a dose dependent manner in primary rat mixed hippocampal cultures (Boggs et al., "Clusterin (Apo J) Protects Against In-Vitro Amyloid-Beta (1-40) Neurotoxicity," *J Neurochem* 67:1324-1327 (1996), which is hereby incorporated by reference in its entirety). In the brains of AD patients, ApoJ mRNA expression is increased two-fold (Oda et al., "Purification and Characterization of Brain Clusterin," *Biochem Biophys Res Commun* 204:1131-1136 (1994), which is hereby incorporated by reference in its entirety) and ApoJ protein expression is elevated about 40% (May et al., "Dynamics Of Gene Expression for a Hippocampal Glycoprotein Elevated in Alzheimer's Disease and in Response to Experimental Lesions in Rat," *Neuron* 5:831-839 (1990), which is hereby incorporated by reference in its entirety) compared to normal controls. The ApoJ 2DE spots marked in FIG. 2 all demonstrated a higher average % volume in AD patients. One previous study indicated no difference in the total ApoJ CSF concentration of AD patients (Lidstrom et al., "Normal Levels of Clusterin in Cerebrospinal Fluid in Alzheimer's Disease, and No Change After Acute Ischemic Stroke," *J Alzheimers Dis* 3:435-442 (2001), which is hereby incorporated by reference in its entirety), while another study found two isoforms of ApoJ to have a decrease in concentration in the CSF of AD patients (Puchades et al., "Proteomic Studies of Potential Cerebrospinal Fluid Protein Markers for Alzheimer's Disease," *Brain Res Mol Brain Res* 118:140-146 (2003), which is hereby incorporated by reference in its entirety).

Example 6

Proteins Involved in Inflammation

One spot in FIG. 2 contains a fragment of the Ig heavy chain and another contains Ig light chains. It has been shown that the serum of AD patients contains autoantibodies (such as antibodies to neurofilaments (Chapman et al., "Alzheimers-Disease Antibodies Bind Specifically To a Neurofilament Protein in Torpedo Cholinergic Neurons," *J Neurosci* 9:2710-2717 (1989), which is hereby incorporated by reference in its entirety)) not contained in the serum of control patients. Also, the basement membrane of the choroid plexus contains deposits of IgG in AD patients (Serot et al., "Comparative Immunohistochemical Characteristics of Human Choroid-Plexus in Vascular and Alzheimers Dementia," *Human Pathol* 25:1185-1190 (1994), which is hereby incorporated by reference in its entirety) and both IgG and light chains (kappa and lambda) were located in the corona of senile plaques consisting of degenerating neurites surrounding amyloid cores (Eikelenboom et al., "Immunoglobulins and Complement Factors in Senile Plaques—An Immunoperoxidase Study," *Acta Neuropathol* 57:239-242 (1982), which is hereby incorporated by reference in its entirety). A study by Blennow et al., using 45 AD patients and 24 healthy controls, found evidence of intrathecal synthesis of immunoglobulins in 26% of the AD patients and in none of the controls (Blennow et al., "Intrathecal Synthesis of Immunoglobulins in Patients with Alzheimer's Disease," *Eur Neuropsychopharmacol* 1:79-81 (1990), which is hereby incorporated by reference in its entirety). The Ig heavy chain spot demonstrated an increase in % volume in AD patients compared to non-AD patients and the position on the gel (MW) and sequence coverage indicate that it contains a C-terminal fragment of the Ig heavy chain. The Ig light chain spot showed a decrease in average % volume in the 2DE gels of CSF from AD patients compared to non-AD patients. The location of the spot (MW and pI) as well as the MS sequence coverage indicates that it contains intact Ig light chain.

The inflammatory related protein plasmin, was also identified in one of the spots in FIG. 2. Plasmin is a proteolytic enzyme involved in a variety of processes and can degrade both monomeric Aβ and Aβ fibrils in vivo (Selkoe D J., "Clearing the Brain's Amyloid Cobwebs," *Neuron* 32:177-180 (2001), which is hereby incorporated by reference in its entirety). Using mouse knockout models, it has been shown that when Aβ is injected into the brains of mice, the plasmin system helps to clear the Aβ and prevent neuronal degeneration (Melchor et al., "The Tissue PlasminoGen Activator-PlasminoGen Proteolytic Cascade Accelerates Amyloid-Beta (A beta) Degradation and Inhibits A Beta-Induced Neurodegeneration," *J Neurosci* 23:8867-8871 (2003), which is hereby incorporated by reference in its entirety). In vitro studies have shown that Aβ can both increase the mRNA expression level (Tucker et al., "The Plasmin System is Induced by and Degrades Amyloid-Beta Aggregates," *J Neurosci* 20:3937-3946 (2000), which is hereby incorporated by reference in its entirety) of plasminogen activators (which cleave plasminogen to create its activated form plasmin) and increase the activators' activity (Tucker et al., "The Plasmin System is Induced by and Degrades Amyloid-Beta Aggregates," *J Neurosci* 20:3937-3946 (2000), which is hereby incorporated by reference in its entirety). The level of plasmin is lower in the hippocampus and cortex of AD patients (Ledesma et al., "Brain Plasmin Enhances APP Alpha-Cleavage and A Beta Degradation and is Reduced in Alzheimer's Disease Brains," *EMBO Rep* 1:530-535 (2000), which is hereby incorporated by reference in its entirety). The plasminogen spot, however, was found have increased expression levels in AD CSF relative to non-AD patients. Based only on the spectra, it cannot be concluded if this spot contains plasminogen or the active plasmin.

Fibrinogen beta was identified in one of the marked spots at a molecular weight of approximately 60 kDa. Fibrinogen monomers polymerize to form fibrin clots and act as cofactors for platelet aggregation. The white matter lesions in the brains of patients with AD and other forms of dementia contain several serum proteins including fibrinogen (Tomimoto et al., "Regressive Changes of Astroglia in White Matter Lesions in Cerebrovascular Disease and Alzheimer's Disease Patients," *Acta Neuropathol* 94:146-152 (1997), which is hereby incorporated by reference in its entirety). Fibrinogen can also bind to and activate plasminogen, which was discussed in the previous paragraph. The fibrinogen spot shows a higher average % volume in AD patients. This increase in fibrinogen beta may be related to the inflammation associated with AD.

The protein in the marked spot at a MW of about 70 kDa contains complement component 3 (C3). C3 is cleaved by C3 convertase to form C3a and C3b. C3b mediates phagocytosis via complement receptors on specialized cells and is also involved in further activation of the complement cascade (Wyss-Coray et al., "Prominent Neurodegeneration and Increased Plaque Formation in Complement-Inhibited Alzheimer's Mice," *Proc Natl Acad Sci USA* 99:10837-10842 (2002), which is hereby incorporated by reference in its entirety). C3b is composed of two chains linked by disulfide bonds. The molecular weight, pI, and amino acid sequence coverage of the spectra for the spot identified as complement component 3 suggests that it contains the beta chain of C3b. The complement system is a significant initiator of inflammation and it has been noted that many of the pathological changes that occur in the AD brain could be caused by the activation of the complement system (Bradt et al., "Complement-Dependent Proinflammatory Properties of the Alzheimer's Disease Beta-Peptide," *J Exp Med* 188:431-438 (1998), which is hereby incorporated by reference in its entirety). In AD patients, C3 is deposited in cerebrovascular amyloidosis lesions (Verbeek et al., "Distribution of A Beta-Associated Proteins in Cerebrovascular Amyloid of Alzheimer's Disease," *Acta Neuropathol* 96:628-636 (1998), which is hereby incorporated by reference in its entirety) and products of the early complement components C1, C4, and C3 are co-localized with diffuse and fibrillar Aβ (Veerhuis et al., "Early Complement Components in Alzheimer's Disease Brains," *Acta Neuropathol* 91:53-60 (1996), which is hereby incorporated by reference in its entirety). In murine models, C3 has an effect on Aβ deposition. An inhibitor of C3 convertase was found to increase Aβ deposition and increased C3 production was found to decrease Aβ deposition (Wyss-Coray et al., "Prominent Neurodegeneration and Increased Plaque Formation in Complement-Inhibited Alzheimer's Mice," *Proc Natl Acad Sci USA* 99:10837-10842 (2002), which is hereby incorporated by reference in its entirety). Previous studies have also suggested that the amount of C3 in the brain is affected by the presence of Aβ. Addition of synthetic Aβ peptides to a culture of microglial cells increased C3 production 5 to 10 fold (Haga et al., "Synthetic Alzheimer Amyloid Beta-a4peptides Enhance Production of Complement C3 Component by Cultured Microglial Cells," *Brain Res* 601:88-94 (1993), which is hereby incorporated by reference in its entirety) and the production of complement proteins has been found to be increased in AD brains (Wyss-Coray et al., "Prominent Neurodegeneration and Increased Plaque Formation in Complement-Inhibited Alzheimer's Mice," *Proc Natl Acad Sci USA* 99:10837-10842 (2002), which is hereby incorporated by reference in its entirety). In agreement with this, the average % volume of the C3 spot was found to be higher in CSF 2DE gels of AD patients.

Example 7

Proteolytic Enzyme Inhibitors

Two spots contained α-1-antitrypsin. The MW and MS amino acid sequence coverage of α-1-antitrypsin-1 indicates that it contains intact protein while that of α-1-antitrypsin-2 suggests a C-terminal fragment. α-1-antitrypsin is the most abundant plasma serine protease inhibitor. Using antibody staining, α-1-antitrypsin has been found in senile plaques and neurofibrillary tangles of AD patients (Gollin et al., "Alpha-1-Antitrypsin and Alpha-1-Antichymotrypsin Are in the Lesions of Alzheimers-Disease," *Neuroreport* 3:201-203 (1992), which is hereby incorporated by reference in its entirety). The reactive loop of α-1-antitrypsin has been shown to readily adopt a β-pleated structure. This may explain the association of α-1-antitrypsin with the amyloid plaques and tau tangles, both of which also have a β-pleated structure (Elliott et al., "Inhibitory Conformation of the Reactive Loop of Alpha(1)-Antitrypsin," *Nat Struct Biol* 3:676-681 (1996), which is hereby incorporated by reference in its entirety). By comparing the plasma proteome of AD and control patients, Yu et al. (u et al., "Aberrant Profiles of Native and Oxidized Glycoproteins in Alzheimer Plasma," *Proteomics* 3:2240-2248 (2003), which is hereby incorporated by reference in its entirety) found that there was a significant increase in native and oxidized forms of glycosylated α-1-antitrypsin in the plasma from AD patients. Puchades et al. also report an increase in the level of two α-1-antitrypsin isoforms in the cerebrospinal fluid of AD patients. The average % volume of α-1-antitrypsin-1 shows a decrease in AD patients while α-1-antitrypsin-2 shows an increase.

ProSAAS is an inhibitor of neuroendocrine convertase 1, an enzyme that mediates the proteolytic cleavage of many peptide precursors. The molecular weight and pI, of the proSAAS marked spot on the 2DE gel indicates that it does not contain intact proSAAS and the sequence coverage from the mass spectrum included peptides corresponding to amino acids 62 to 216. The molecular weight, pI, and spectra are consistent with a fragment known to be produced by the cleavage of proSAAS with furin that has a predicted amino acid sequence coverage of 61-220. An N-terminal peptide of proSAAS has been shown to be in the tau inclusions of AD and Pick's disease (Wada et al., "A Human Granin-Like Neuro endocrine Peptide Precursor (proSAAS) Immunoreactivity in Tau Inclusions of Alzheimer's Disease and Parkinsonism-Dementia Complex on Guam," *Neurosci Lett* 356:49-52 (2004), which is hereby incorporated by reference in its entirety) and the CSF concentration of proSAAS has been found to be lower in patients with frontotemporal dementia (Davidsson et al., "Studies of the Pathophysiological Mechanisms in Frontotemporal Dementia by Proteome Analysis of CSF Proteins," *Brain Res Mol Brain Res* 109:128-133 (2002), which is hereby incorporated by reference in its entirety). The proSAAS spot marked in FIG. 2 shows a lower average % volume in AD patients.

Example 8

Neuronal Membrane Proteins

Contactin (also known as neural cell surface protein F3) is a glycosyl phosphatidylinositol-anchored neural cell adhesion molecule. Contactin plays a role in communication between neuron and glial cells. It contributes to pathways involved in neurite outgrowth, myelination, and oligodendrocyte development (Hu et al., "F3/Contactin Acts as a Functional Ligand for Notch During Oligodendrocyte Maturation," *Cell* 115:163-175 (2003), which is hereby incorporated by reference in its entirety). The contactin spot has a lower average % volume in gels from AD patients. The molecular weight and sequence coverage suggest that the spot contains a fragment of contactin.

The exact function of neuronal pentraxin receptor (NPR) is unknown, although it has been suggested to be involved in the clearance of synaptic debris as synapses are formed or remodeled. It is moderately abundant in the brain, with the highest expression levels being in the cerebellum and hippocampus. The C-terminal end of NPR has homology (22-25% identity) to classical pentraxins such as C-reactive protein and serum amyloid P protein (Dodds et al., "Neuronal Pentraxin Receptor, a Novel Putative Integral Membrane Pentraxin That Interacts With Neuronal Pentraxin 1 and 2 and Taipoxin-Associated Calcium-Binding Protein 49," *J Biol Chem* 272:21488-21494 (1997), which is hereby incorporated by reference in its entirety). The average % volume of the NPR/Transthyretin spot is lower in gels from AD patients.

Although this discussion has focused on each of the spots individually, it should be reiterated that the RF method uses the % volume information from all of the spots together to classify the 2DE gels. Using a combination of variables to classify the samples is the strength of multivariate methods of analysis such as RF. Also, as shown in FIG. 5, the spots do not contribute equally to the classification. Some spots, such as the ND-3 and the α-1-antitrypsin-2 isoforms, contribute more to a correct classification than others. This does not imply, however, that the ApoJ-3 spot with the lowest z-score in the set is unimportant to the gel classification. This study is based on using all 23 spots and removing the ApoJ-3 spot decreases the sensitivity.

Here, the RF analysis was performed with the goal of minimizing the total number of misclassified samples. Therefore, to maximize both the sensitivity and specificity, the cost of misclassifying an AD sample was assumed to be equal to the cost of misclassifying a non-AD sample. There are situations, however, where the sensitivity of a diagnostic method is more important than the specificity (or vice versa). In these cases, the results of the analysis shown in FIG. 6A could be used to determine a cut off value for the misclassification cost ratio that could be used to achieve the desired sensitivity and specificity.

The sensitivity and specificity combinations derived from the ROC analysis of FIG. 6B result in an area under the ROC curve (AUC) of 0.96. This value is higher than those reported in several recent studies investigating the use of CSF Tau (AUC=0.937, (73)), $AB_{42}$ (AUC=0.926, (Lewczuk et al., "Neurochemical Diagnosis of Alzheimer's Dementia by CSF A Beta 42, A Beta 42/A Beta 40 Ratio and Total Tau," *Neurobiol Aging* 25:273-281 (2004), which is hereby incorporated by reference in its entirety)), phosphorylated tau (AUC=0.887, (Maddalena et al., "Biochemical Diagnosis of Alzheimer Disease by Measuring the Cerebrospinal Fluid Ratio of Phosphorylated Tau Protein to Beta-Amyloid Peptide(42)," *Arch Neurol* 60:1202-1206 (2003), which is hereby incorporated by reference in its entirety)), ratio of $A\beta_{42}$ to phosphorylated tau (AUC=0.934, (Maddalena et al., "Biochemical Diagnosis of Alzheimer Disease by Measuring the Cerebrospinal Fluid Ratio of Phosphorylated Tau Protein to Beta-Amyloid Peptide(42)," *Arch Neurol* 60:1202-1206 (2003), which is hereby incorporated by reference in its entirety)), and the ratio of $AB_{42}/AB_{1-40}$ (AUC=0.951, (Lewczuk et al., "Neurochemical Diagnosis of Alzheimer's Dementia by CSF A Beta 42, A Beta 42/A Beta 40 Ratio and Total Tau," *Neurobiol Aging* 25:273-281 (2004), which is hereby incorporated by reference in its entirety)) to discriminate between a group of AD patients and a group of control patients without dementia. Also, the reported AUC's decreased when patients with dementia were included in the analyses (Clark et al., "Cerebrospinal Fluid Tau and Beta-Amyloid—How Well Do These Biomarkers Reflect Autopsy-Confirmed Dementia Diagnoses?," *Arch Neurol* 60:1696-1702 (2003), Lewczuk et al., "Neurochemical Diagnosis of Alzheimer's Dementia by CSF A Beta 42, A Beta 42/A Beta 40 Ratio and Total Tau," Neurobiol Aging 25:273-281 (2004); Maddalena et al., "Biochemical Diagnosis of Alzheimer Disease by Measuring the Cerebrospinal Fluid Ratio of Phosphorylated Tau Protein to Beta-Amyloid Peptide(42)," *Arch Neurol* 60:1202-1206 (2003), which are hereby incorporated by reference in their entirety).

Using 2DE, the proteomes of pathologically validated AD CSF samples and non-AD CSF samples that included several appropriate neurological controls were studied. The random forest multivariate statistical method identified a panel of 23 2DE CSF spots that gave high specificity and sensitivity in the antemortem differential diagnosis of AD. The proteins identified in these spots are functionally related to Aβ transport, inflammation, and proteolytic activity in CSF or are present on neuronal membranes. The method presented has shown promising results and the next step in this investigation is to validate the results using alternative techniques such as immunoassays. These results should also be tested using a broader and more diverse sample population to get a more accurate estimate of the prediction error. Nonetheless, this multivariate statistical study represents the largest cohort of pathologically characterized antemortem CSF samples used in an AD proteomic biomarker study published to date and suggests the possibility of developing clinically relevant diagnostic assays based on a proteomic analysis.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A method comprising:
   providing one or more cerebrospinal fluid test samples from a subject comprising at least 8 proteins selected from albumin, alpha-1-antitrypsin, apolipoprotein E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein;
   contacting the one or more cerebrospinal fluid test samples with reagents selected from the group consisting of antibodies, aptamers, and combinations thereof specific to each of the at least 8 proteins to form at least 8 different protein-reagent complexes;
   detecting the at least 8 different protein-reagent complexes; and
   quantifying the relative levels of each of the at least 8 proteins in the test sample(s) based on detection of the at least 8 different protein-reagent complexes.

2. The method of claim 1, wherein the one or more cerebrospinal fluid test samples are cerebrospinal fluid samples from individuals diagnosed with Alzheimer's disease.

3. The method of claim 2, wherein the one or more cerebrospinal fluid test samples are antemortem cerebrospinal fluid samples from individuals diagnosed with Alzheimer's disease and wherein the individual's Alzheimer's disease diagnosis is confirmed postmortem.

4. The method of claim 1, wherein the one or more cerebrospinal fluid test samples are cerebrospinal fluid samples from individuals diagnosed as not having Alzheimer's disease.

5. The method of claim 4, wherein the one or more cerebrospinal fluid test samples are antemortem cerebrospinal fluid samples from individuals diagnosed as not having Alzheimer's disease and wherein the individual's diagnosis as not having Alzheimer's disease is confirmed postmortem.

6. The method according to claim 1, wherein relative levels of said at least 8 proteins are determined as % volume relative levels.

7. The method of claim 1, wherein said method is carried out using an immunoassay.

8. The method of claim 1, wherein said one or more reagents are antibodies.

9. The method of claim 1, wherein said one or more reagents are aptamers.

10. The method of claim 1, wherein said one or more reagents are a combination of antibodies and aptamers.

11. A method for aiding in the diagnosis of a subject as having Alzheimer's disease, the method comprising:
    obtaining a cerebrospinal fluid test sample from a subject;
    analyzing the cerebrospinal fluid test sample from the subject to quantify relative levels of at least 8 proteins in the test sample selected from albumin, alpha-1-antitrypsin, apolipoprotein E, apolipoprotein J, complement component 3, contactin, fibrin beta, Ig heavy chain, Ig light chain, neuronal pentraxin receptor, plasminogen, proSAAS, retinol-binding protein, transthyretin, and vitamin D binding protein, wherein said analyzing comprises selectively measuring the levels of the at least 8 proteins in the sample using a multiple reaction monitoring mass spectrometry; and comparing said analyzed relative levels of said proteins in the test sample(s) to relative levels of said proteins in a control using a multivariate statistical analysis, wherein a statistically significant similarity in the relative levels of said proteins in the test sample as compared to the control is indicative of Alzheimer's disease.

\* \* \* \* \*